United States Patent [19]
Xia et al.

[11] Patent Number: 5,891,871
[45] Date of Patent: Apr. 6, 1999

[54] SUBSTITUTED 2,3-BENZODIAZEPIN-4-ONES AND THE USE THEREOF

[75] Inventors: Haiji Xia; Sui Xiong Cai, both of Foothill Ranch; George Field, Santa Ana; Nancy C. Lan, S. Pasadena; Yan Wang, Irvine, all of Calif.

[73] Assignee: CoCensys, Inc., Irvine, Calif.

[21] Appl. No.: 821,638

[22] Filed: Mar. 20, 1997

Related U.S. Application Data

[60] Provisional application No. 60/013,813, Mar. 21, 1996.

[51] Int. Cl.$^6$ .......................... A61K 31/55; C07D 243/10
[52] U.S. Cl. .......................... 514/219; 514/220; 514/221; 540/493; 540/495; 540/500
[58] Field of Search .................................. 540/493, 495, 540/500; 514/219, 220, 221

[56] References Cited

U.S. PATENT DOCUMENTS

| | | | |
|---|---|---|---|
| 4,614,740 | 9/1986 | Láng et al. | 514/221 |
| 4,835,152 | 5/1989 | Kőrösi et al. | 514/220 |
| 5,550,124 | 8/1996 | Gee | 514/221 |

FOREIGN PATENT DOCUMENTS

| | | |
|---|---|---|
| 0 492 485 A1 | 7/1992 | European Pat. Off. . |
| 2085645 | 2/1972 | France . |
| 2104998 | 5/1972 | France . |
| WO 94/13275 | 6/1994 | WIPO . |
| WO 97/28135 | 8/1997 | WIPO . |

OTHER PUBLICATIONS

Anderson, B.A. et al., "Application of a Practical Biocatalytic Reduction to an Enantioselective Synthesis of the 5H–2,3–Benzodiazepine LY300164," *J. Am. Chem. Soc.* 117:12358–12359 (Dec. 1995).

Buchan, A.M. et al., "AMPA Antagonists: Do They Hold More Promise for Clinical Stroke Trials Than NMDA Antagonists?" *Stroke* 24(Suppl. I):I–148–I–152 (1993).

De Sarro, G. et al., "GYKI 52466 and related 2,3–benzodiazepines as anticonvulsant agents in DBA/2 mice," *Eur. J. Phamacol.* 294:411–422 (Dec. 1995).

Gatta, F. et al., "Derivatives of 2,3–Benzodiazepine," *IL Farmaco–Ed. Sc.* 40:942–955 (1985).

Keana, J.F.W. et al., "Synthesis and Structure–Activity Relationships of Substituted 1,4–Dihydroquinoxaline–2,3–diones: Antagonists of N–Methyl–D–aspartate (NMDA) Receptor Glycine Sites and Non–NMDA Glutamate Receptors," *J. Med. Chem.* 38:4367–4379 (Oct. 1995).

Larson, J. et al., "Effects of an AMPA receptor modulator on methamphetamine–induced hyperactivity in rats," *Brain Res.* 738:353–356 (Nov. 1996).

Sheardown, M.J. et al., "AMPA, but not NMDA, receptor antagonism is neuroprotective in gerbil global ischaemia, even when delayed 24 h," *Eur. J. Pharm.* 236:347–353 (1993).

Staubli, U. et al., "Facilitation of glutamate receptors enhances memory," *Proc. Natl. Acad. Sci. USA* 91:777–781 (1994).

Thomas, R.J., "Excitatory Amino Acids in Health and Disease," *JAGS* 43:1279–1289 (Nov. 1995).

Bennett, M.V.L. et al., "The GluR2 Hypothesis: Ca$^{++}$–permeable AMPA Receptors in Delayed Neurodegeneration," *Cold Spring Harbor Symposia on Quantitative Biology* LXI:373–384 (Jun. 1996).

Blin, O., "Should N–Methyl–D–Aspartate or Non–N–Methyl–D–Aspartate Glutamate Receptor Antagonists Be Used in Amyotrophic Lateral Sclerosis?," in: *Pathogenesis and Therapy of Amyotrophic Lateral Sclerosis*, Serratrice, G. and T. Musat, eds., Lippincott–Raven Publishers, Philadelphia, PA, pp. 259–261 (1995).

Graham, S.H. et al., "A Dose–Response Study of Neuroprotection Using the AMPA Antagonist NBQX in Rat Focal Cerebral Ischemia," *J. Pharmacology & Exper. Therapeutics* 276:1–4 (Jan. 1996).

Hunter, J.C. and L. Singh, "Role of excitatory amino acid receptors in the mediation of the nociceptive response to formalin in the rat," *Neurosci. Letters* 174:217–221 (1994).

Johnson, S.A. et al., "Antagonism of Methamphetamine–Induced Hyperactivity in Rats by Specific Facilitation of AMPA–Receptor–Mediated Glutamatergic Transmission," *Soc. Neurosci.* 22:1676, Abstract No. 657.12 (1996).

Karcz–Kubicha, M. and S. Liljequist, "Evidence for an anxiogenic action of AMPA receptor antagonists in the plus–maze test," *Eur. J. Pharmacol.* 279:171–177 (Jun. 1995).

Lynch, G. et al., "Evidence That a Positive Modulator of AMPA–Type Glutamate Receptors Improves Delayed Recall in Aged Humans," *Exper. Neurol.* 145:89–92 (May 1997).

(List continued on next page.)

*Primary Examiner*—Mukund J. Shah
*Assistant Examiner*—Brenda Coleman
*Attorney, Agent, or Firm*—Sterne, Kessler Goldstein & Fox P.L.L.C.

[57] ABSTRACT

The invention relates to substituted 2,3-benzodiazepin-4-ones which are antagonists or positive modulators of AMPA receptors, and the use thereof for treating, preventing or ameliorating neuronal loss associated with stroke, global and focal ischemia, CNS trauma, hypoglycemia and surgery, as well as treating or ameliorating neurodegenerative diseases including Alzheimer's disease, amyotrophic lateral sclerosis, Huntington's disease, Parkinson's disease and Down's syndrome, treating, preventing or ameliorating the adverse consequences of the overstimulation of the excitatory amino acids, treating or ameliorating anxiety, psychosis, convulsions, chronic pain, glaucoma, CMV retinitis, urinary incontinence, muscular spasm and inducing anesthesia, as well as for treating or ameliorating the adverse consequences of excitatory amino acid deficiency such as schizophrenia, Alzheimer's disease and malnutrition and neural maldevelopment, and as cognition enhancers. The invention also is directed to the process for the preparation of the substituted 2,3-benzodiazepin-4-ones.

41 Claims, No Drawings

OTHER PUBLICATIONS

Palmer, L.C. et al., "Evidence That Positive Modulators of AMPA Receptors Increase Aggregate Neuronal Activity in Neocortex Relative to Striatum: Relevance to Schizophrenia," *IBC's Second Intl. Symposium on Schizophrenia: Latest Advances in Understanding and Drug Development*, Philadelphia, PA (Jun. 1996).

Schuller, J.J. and J.F. Marshall, "Intrastriatal DNQX induces rotation and pallidal Fos in the 6–OHDA model of Parkinson's disease," *NeuroReport 6*:2594–2598 (Dec. 1995).

Yamakura, T. et al., "The sensitivity of AMPA–selective glutamate receptor channels to pentobarbital is determined by a single amino acid residue of the α2 subunit," *FEBS Letters 374*:412–414 (Nov. 1995).

Yoshiyama, M. et al., "Effects of GYKI 52466 and CNQX, AMPA/kainate receptor antagonists, on the micturition reflex in the rat," *Brain Res. 691*:185–194 (Sep. 1995).

Gatta et al., Chromium Trioxide Oxidation Products From 4–Spiro–1–Phenylisochromans, Journal of Heteocyclic Chemistry, vol. 20, No. 5, pp. 1267–1270, Sep. 1983.

Tomori et al., Pharmacokinetic and Metabolism Studies on Girisopam by Chromatographic and Spectrometric Methods in Humans, Journal of Chromatography, vol. 578, pp. 91–101, 1992.

Pelaggi et al., Electronic and Conformational Properties of 2,3–Benzodiazepine Derivatives, STN Printout, 1996.

Flammang, 2,3–Benzodiazepines: 2–Amino–3–Isoquinolinones From Ring Contraction of 4–oxo–2,3–Benzodiazepines, STN Printout, 1980.

Flammang et al., 2,3–Benzodiazepine Systems, STN Printout, 1976.

Nagarajan et al., Derivatives of 3,5–dihydro–4H–benzo[2,3]diazepin–4–one, STN Printout, 1972.

Beal, Aging, Energy, and Oxidative Stress in Neurodegenerative Diseases, Ann. Neurol., vol. 38, pp. 357–366, 1995.

SUBSTITUTED 2,3-BENZODIAZEPIN-4-ONES AND THE USE THEREOF

This application claims benefit of U.S. provisional application Ser. No. 60/013,813 filed Mar. 21, 1996.

BACKGROUND OF THE INVENTION

1. Field of the Invention

This invention is in the field of medicinal chemistry. In particular, the invention relates to novel substituted 2,3-benzodiazepin-4-ones. These analogs are antagonists of α-amino-3-hydroxy-5-methylisoxazole-4-propionic acid (AMPA) ionotropic receptors. Certain of these analogs are positive modulators of AMPA receptors. The invention also is directed to the use of these substituted 2,3-benzodiazepin-4-ones for the treatment of neuronal damage following global and focal ischemia, and for the treatment or prevention of neurodegenerative conditions, as anticonvulsants and as cognitive enhancers and for the treatment of schizophrenia and pain. The invention is also directed to the process for the preparation of the substituted 2,3-benzodiazepin-4-ones.

2. Related Background Art

Excitatory amino acid receptors are classified into two general types. Receptors that are directly coupled to the opening of cation channels in the cell membrane of the neurons are termed "ionotropic." This type of receptor has been subdivided into at least three subtypes, which are defined by the depolarizing actions of the selective agonist N-methyl-aspartate (NMDA), α-amino-3-hydroxy-5-methyoisoxazole-4-propionic acid (AMPA), and kainic acid (KA). The second general type is the G-protein or second messenger-linked "metabotropic" excitatory amino acid receptor. This second type, when activated by the agonists quisqualate, ibotenate, or trans-1-aminocyclopentane-1,3-dicarboxylic acid, leads to enhanced phosphoinositide hydrolysis in the postsynaptic cell. Both types of receptors appear not only to mediate normal synaptic connections during development, but also changes in the efficiency of synaptic transmission throughout life. See Schoepp, Bockaert, and Sladeezek, *Trends Pharm. Sci.* 11: 508 (1990); McDonald and Johnson, *Brain Res. Rev.* 15: 41 (1990). The excessive or inappropriate stimulation of excitatory amino acid receptors leads to neuronal cell damage or loss by way of a mechanism known as excitotoxicity. The medical consequences of such neuronal degeneration makes the abatement of these degenerative neurological processes an important therapeutic goal. See U.S. Pat. No. 5,284,957.

Antagonists of the AMPA receptor are considered useful in treating, preventing and ameliorating a number of neurologic disorders which are due to overstimulation by the excitatory amino acids. These include acute neurologic disorders such as domoic acid poisoning; cerebral ischemia, global ischemia associated with cardiac arrest; stroke; spinal cord trauma; hypoxia; anoxia; poisoning by carbon monoxide, manganese or cyanide; hypoglycemia; mechanical trauma to the nervous system, epileptic seizures; and chronic neurologic disorders such as Huntington's disease, neuronal injury associated with HIV and AIDS, AIDS dementia, neuropathic pain syndrome, olivopontocerebral atrophy, Parkinson's disease, amyotrophic lateral sclerosis, mitochondrial abnormalities, Alzheimer's disease, hepatic encephalopathy, Tourette's syndrome, schizophrenia, and drug addiction (see Lipton and Rosenberg, *N. Engl. J. Med.* 330: 613–622 (1994)).

Positive modulators of AMPA receptors are expected to be useful for the treatment or amelioration of a number of chronic neurologic disorders, such as schizophrenia, Alzheimer's disease and malnutrition and neural maldevelopment (Thomas, R. J., *J. Am. Geriatr. Soc.* 43: 1279–1289 (1995)). It has been shown that the AMPA receptor positive modulator BDP 1-(1,3-benzodioxol-5-ylcarbonyl) piperidine and its derivatives enhance memory (Staubli et al., *Proc. Natl. Acad. Sci.* 91: 777–778 (1994)). The AMPA positive modulator BDP-29 has been shown to attenuate the amount of stereotypic rearings seen in rats after methamphetamine injection, suggesting that AMPA receptor modulators might be useful for the treatment of schizopherenia (Larson et al., *Brain Res.* 738, 353–356 (1996)).

Recent studies have shown that AMPA receptor antagonists are neuroprotective in focal and global ischemia models. The competitive AMPA receptor antagonist NBQX (2,3-dihydroxy-6-nitro-7-sulfamoylbenzo[f]quinoxaline) has been reported to be effective in preventing global and focal ischemic damage. See Sheardown et al., *Science* 247: 571 (1990); Buchan et al., *Neuroreport.* 2:473 (1991); Lepeillet et al., *Brain Res.* 571:115 (1992). The noncompetitive AMPA receptor antagonist GKYI 52466 (1-(4-aminophenyl)- 4-methyl-7,8-methylenedioxy-5H-2,3-benzodiazepine-hydrochloride) has been shown to be an effective neuroprotective agent in rat global ischemia models. See Lapeillet et al., *Brain Res.* 571: 115 (1992). GYKI 52466 has also been shown to be an effective anticonvulsant. See DeSarro et al., *Eur. J. Pharmacol.* 294: 411 (1995). These studies strongly suggest that the delayed neuronal degeneration in brain ischemia involves glutamate excitotoxicity mediated at least in part by AMPA receptor activation. Thus, AMPA receptor antagonists are expected to prove useful as neuroprotective agents and improve the neurological outcome of cerebral ischemia in animals. See U.S. Pat. No. 5,284,957.

Anderson et. af., *J. Am. Chem. Soc.* 117. 12358–12359 (1995) reported the synthesis of 5-H-2,3-benzodiazepine (LY300164) shown below. The compound is said to be a noncompetitive antagonist of AMPA receptors with anticonvulsant activity.

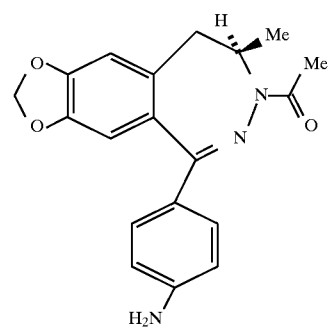

U.S. Pat. No. 4,614,740 discloses 2,3-benzodiazepines with general formula:

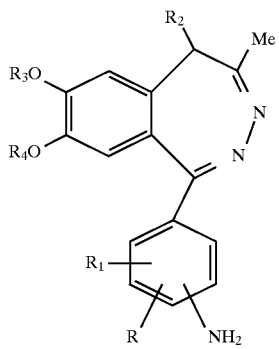

wherein R and $R_1$ each represent hydrogen, chlorine, $C_{1-4}$ alkyl or $C_{1-4}$ alkoxy, $R_2$ stands for hydrogen or $C_{1-4}$ alkyl, $R_3$ and $R_4$ each denote $C_{1-4}$ alkyl, or combined they denote methylene. These compounds are said to possess valuable central nervous effect and in particular exert antiaggressive, anxiolytic, narcosis potentiating and soporific properties.

U.S. Pat. No. 4,835,152 discloses the preparation of 2,3-benzodiazepine:

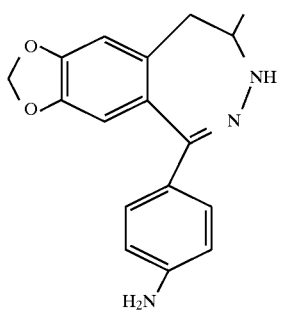

This compound is said to possess CNS stimulating activity.

EP patent application 0492485 discloses 2,3-benzodiazepines with the following formula:

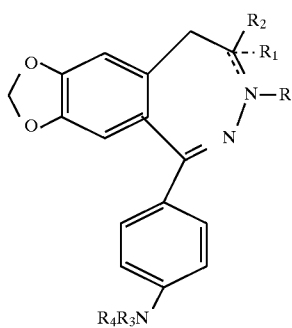

wherein R stands for a $C_{1-6}$ aliphatic acyl group, optionally substituted by a methoxy, cyano, carboxyl amino, $C_{1-4}$ alkylamino, di($C_{1-4}$ alkyl)amino, pyrrolidino, phthalimido or phenyl, or by one or more halogens, or R is a benzoyl, cyclopropanecarbonyl, $C_{1-5}$ alkylcarbamoyl or phenylcarbamoyl, or R is absent when a double bond exists between the N(3) and C(4) atoms; $R_1$ is hydrogen or absent when a double bond exists between the N(3) and C(4) atoms; $R_2$ is a $C_{1-3}$ alkyl group or $R_1$ and $R_2$ together stand for a methylene group and no double bond is present between the N(3) and C(4) atoms; $R_3$ is hydrogen or a $C_{1-4}$ aliphatic acyl group; $R_4$ is hydrogen, a $C_{1-6}$ aliphatic acyl group optionally substituted by a methoxy, cyano, carboxy, amino, $C_{1-4}$ alkylamino, di($C_{1-4}$ alkyl)amino, pyrrolidino, phthalimido or phenyl group or by one or more halogen; as well as a benzoyl, palmitoyl, cyclopropanecarbonyl, $C_{1-5}$ alkylcarbamoyl or phenylcarbamoyl group. These compounds are said to possess valuable central nervous system effects, particularly muscle-relaxant, anticonvulsive and neuroprotective action.

Sarro et al, *Eur. J. Pharmacol.*, 294. 411–422 (1995) discloses the following 2,3-benzodiazepines (a-d)

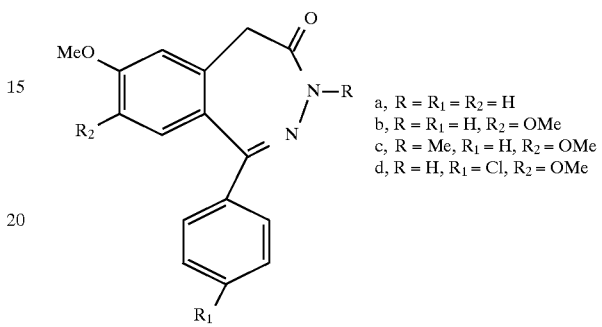

a, R = $R_1$ = $R_2$ = H
b, R = $R_1$ = H, $R_2$ = OMe
c, R = Me, $R_1$ = H, $R_2$ = OMe
d, R = H, $R_1$ = Cl, $R_2$ = OMe

These compounds are said to be anticonvulsant agents in DBA/2 mice.

SUMMARY OF THE INVENTION

This invention is related to substituted 2,3-benzodiazepin-4-ones represented by formula I.

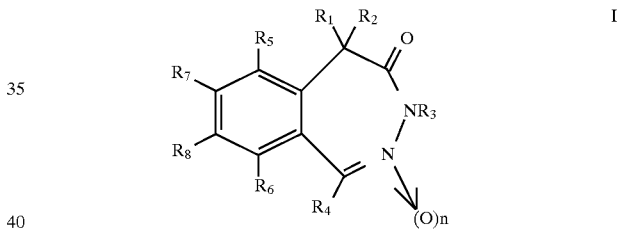

or a pharmaceutically acceptable salt or prodrug thereof, wherein:

$R_1$ and $R_2$ are independently hydrogen, alkyl, haloalkyl, aryl, fused aryl, a carbocyclic group, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, aminoalkyl or thioalkyl; or $R_1$ and $R_2$ are taken together to form a carbocycle or heterocycle;

$R_3$ is hydrogen, alkyl, haloalkyl, aryl, fused aryl, a carbocyclic group, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, aminoalkyl, COR, $CO_2R$ and $CONR_xR_y$, wherein R, $R_x$ and $R_y$ are independently hydrogen, alkyl, haloalkyl, aryl, fused aryl, carbocyclic, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl or aminoalkyl; or $R_x$ and $R_y$ are taken together to form a carbocycle or heterocycle;

$R_4$ is substituted or unsubstituted aryl, fused aryl, a carbocyclic group, a heterocyclic group, or a heteroaryl group;

$R_5$ and $R_6$ are independently hydrogen, halo, haloalkyl, aryl, fused aryl, a carbocyclic group, a heterocyclic group, a heteroaryl group, alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, nitro, amino, cyano, acylamido, hydroxy, thiol, acyloxy, azido, alkoxy, carboxy, carbonylamido or alkylthiol;

$R_7$ and $R_8$ are independently hydrogen, halo, haloalkyl, aryl, fused aryl, a carbocyclic group, a heterocyclic group, a heteroaryl group, alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, nitro, amino, cyano, acylamido, hydroxy, thiol, acyloxy, azido, alkoxy, carboxy, carbonylamido or alkylthiol; or $R_7$ and $R_8$ are taken together to form a carbocycle or heterocycle, for example, $-OCH_2O-$, $-(CH_2)_3-$, $-(CH_2)_4-$, $-OCH_2CH_2O-$, $-CH_2N(R)CH_2-$, $-CH_2CH_2N(R)CH_2-$, $-CH_2N(R)CH_2CH_2-$, $-N(Me)-C(O)-O-$ and $-N=C-C=N-$, wherein R is a defined above; and n is 0 or 1.

The invention also relates to the discovery that the substituted 2,3-benzodiazepin-4-ones represented by Formula I are antagonists of AMPA receptors. Therefore the invention is related to a method of treating, preventing or ameliorating neuronal loss associated with stroke, global and focal ischemia, CNS trauma, hypoglycemia and surgery, spinal cord trauma, neuronal damage associated with cardiac arrest; as well as treating or ameliorating neurodegenerative diseases including Alzheimer's disease, amyotrophic lateral sclerosis, Huntington's disease, Parkinson's disease and Down's syndrome; treating, preventing or ameliorating the adverse consequences of the overstimulation of the excitatory amino acids; treating or ameliorating anxiety, schizophrenia, convulsions, chronic pain, migraine headache, muscle spasm and inducing anesthesia; as well as treating or ameliorating glaucoma and preventing opiate tolerance, comprising administering to an animal in need of such treatment an effective amount of the AMPA receptor antagonists of the present invention, or a pharmaceutically acceptable salt or prodrug thereof.

The invention also relates to the discovery that certain of the substituted 2,3-benzodiazepin-4-ones represented by Formula I are positive modulator of the AMPA receptor. Therefore these compounds can be used to treat or ameliorate the adverse consequences of hypostimulation of the excitatory amino acids, as cognitive enhancer for the treatment of neurodegenerative diseases including Alzheimer's disease, amyotrophic lateral sclerosis, Huntington's disease, Parkinson's disease and Down's syndrome, to treat or ameliorate malnutrition and neural maldevelopment, as well as for the treatment of schizophrenia, by administering to an animal in need of such treatment an effective amount of the AMPA receptor modulators of the present invention, or a pharmaceutically acceptable salt or prodrug thereof.

The invention is also related to a method for the preparation of the compound of formula I comprising the steps of:

(a) reacting, in the presence of a catalyst, a compound of Formula II

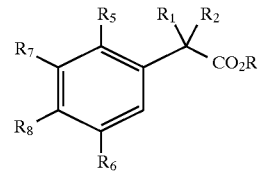

wherein the catalyst can be Lewis acid such as $SnCl_4$ or $P_2O_5$, and R is lower alkyl such as Me or Et, and $R_1-R_2$, $R_5-R_8$ are as defined previously in Formula I, with a compound of Formula III

wherein X is OH or halogen such as Cl, and $R_4$ is as defined previously in Formula I, to afford a compound of Formula IV

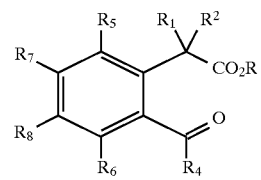

wherein $R_1-R_2$, $R_4-R_8$ and R are as defined previously in Formulae I and II; and (b) reacting the compound of Formula IV with $H_2NNHR_3$, wherein $R_3$ is as previously defined, to afford the compound of Formula I;

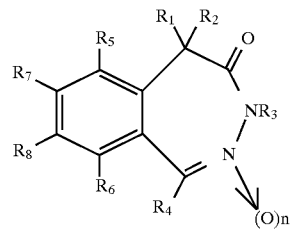

wherein $R_1-R_8$ is as previously defined, n=0, and (c) when $R_3$ is hydrogen, reacting a compound of Formula I with $XR_3$, wherein X is a leaving group such as I, Br, Cl, in the presence of a base, such as NaH or $K_2CO_3$, to afford a compound of Formula I wherein $R_3$ is not hydrogen.

(d) when n=0, reacting a compound of formula I with $H_2O_2$ or peracid such as m-chloroperbenzoic acid, to afford a compound of formula I wherein n=1.

DETAILED DESCRIPTION OF THE INVENTION

The substituted 2,3-benzodiazepin-4-ones are represented by previously defined Formula I. Generally, preferred structures of the substituted 2,3-benzodiazepin-4-ones are where $R_7$ and $R_8$ taken together to form a carbocycle or heterocycle, and $R_4$ is substituted or unsubstituted aryl or heteroaryl. Specifically, preferred structures of the substituted 2,3-benzodiazepin-4-ones are represented by Formulae V–IX. In particular, a preferred embodiment is represented by Formula V:

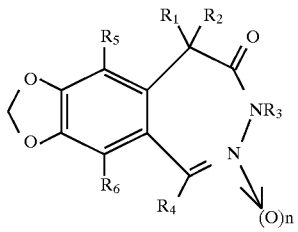

or a pharmaceutically acceptable salt or prodrug thereof wherein $R_1$–$R_6$ and n are as defined previously with respect to Formula I.

Another preferred embodiment of the substituted 2,3-benzodiazepin-4-ones are represented by Formula VI:

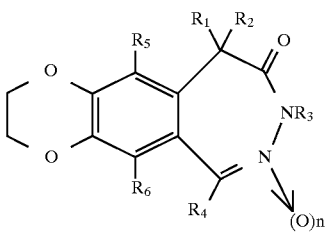

or a pharmaceutically acceptable salt or prodrug thereof wherein $R_1$–$R_6$ and n are as defined previously with respect to Formula I.

Yet another preferred embodiment of the substituted 2,3-benzodiazepin-4-ones are represented by Formula VII:

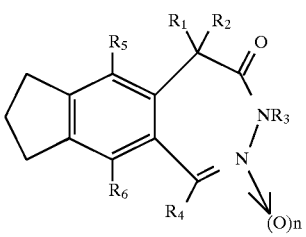

or a pharmaceutically acceptable salt or prodrug thereof wherein $R_1$–$R_6$ and n are as defined previously with respect to Formula I.

Yet another preferred embodiment of the substituted 2,3-benzodiazepin-4-ones are represented by Formula VIII:

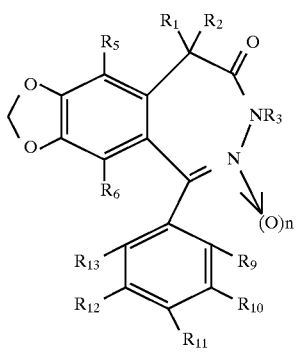

or a pharmaceutically acceptable salt or prodrug thereof wherein $R_1$–$R_3$, $R_5$–$R_6$ and n are as defined previously with respect to Formula I; and $R_9$–$R_{13}$ are independently hydrogen, halo, haloalkyl, aryl, fused aryl, a carbocyclic group, a heterocyclic group, a heteroaryl group, alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, nitro, amino, cyano, acylamido, hydroxy, thiol, acyloxy, azido, alkoxy, carboxy, carbonylamido or alkylthiol; or $R_{10}$ and $R_{11}$ are taken together to form a carbocycle or heterocycle, including —$OCH_2O$—, —$(CH_2)_3$—, —$(CH_2)_4$—, —$OCH_2CH_2O$—, —$CH_2N(R)CH_2$—, —$CH_2CH_2N(R)CH_2$—, —$CH_2N(R)CH_2CH_2$—, or —$N=C$—$C=N$—, wherein R is as defined with respect to Formula I.

With respect to the formulae above:

Typical $C_{6-14}$ aryl groups include phenyl, naphthyl, phenanthryl, anthracyl, indenyl, azulenyl, biphenyl, biphenylenyl and fluorenyl groups.

Typical carbocyclic groups include cyclopropyl, cyclobutyl, cyclopentyl, cyclohexyl, and cycloheptyl groups.

Typical halo groups include fluorine, chlorine, bromine and iodine.

Typical $C_{1-10}$ alkyl groups include methyl, ethyl, propyl, isopropyl, butyl, sec.-butyl, tert.-butyl, 3-pentyl, hexyl and octyl groups. Also contemplated is a trimethylene group substituted on two adjoining positions on the benzene ring of the compounds of the invention.

Typical $C_{2-4}$ alkenyl groups include ethenyl, propenyl, isopropenyl, butenyl, and sec.-butenyl.

Typical $C_{2-4}$ alkynyl groups include ethynyl, propynyl, 1-butynyl, and 2-butynyl groups.

Typical arylalkyl groups include any of the above-mentioned $C_{1-10}$ alkyl groups substituted by any of the above-mentioned $C_{6-14}$ aryl groups.

Typical arylalkenyl groups include any of the above-mentioned $C_{2-4}$ alkenyl groups substituted by any of the above-mentioned $C_{6-14}$ aryl groups.

Typical arylalkynyl groups include any of the above-mentioned $C_{2-4}$ alkynyl groups substituted by any of the above-mentioned $C_{6-14}$ aryl groups.

Typical carbocycloalkyl groups include any of the above-mentioned $C_{1-10}$ alkyl groups substituted by any of the above-mentioned carbocyclic groups.

Typical haloalkyl groups include $C_{1-10}$ alkyl groups substituted by one or more fluorine, chlorine, bromine or iodine atoms, e.g. fluoromethyl, difluoromethyl, trifluoromethyl, pentafluoroethyl, 1,1-difluoroethyl and trichloromethyl groups.

Typical hydroxyalkyl groups include $C_{1-10}$ alkyl groups substituted by hydroxy, e.g. hydroxymethyl, hydroxyethyl, hydroxypropyl and hydroxybutyl groups.

Typical alkoxy groups include oxygen substituted by one of the $C_{1-10}$ alkyl groups mentioned above.

Typical alkylthio groups include sulphur substituted by one of the $C_{1-10}$ alkyl groups mentioned above.

Typical acylamino groups include any $C_{1-6}$ acyl (alkanoyl) substituted on nitrogen, e.g. acetamido, propionamido, butanoylamido, pentanoylamido, hexanoylamido as well as aryl-substituted $C_{2-6}$ substituted acyl groups.

Typical acyloxy groups include any $C_{1-6}$ acyloxy groups, e.g. acetoxy, propionoyloxy, butanoyloxy, pentanoyloxy, hexanoyloxy and the like.

Typical heterocyclic groups include tetrahydrofuranyl, pyranyl, piperidinyl, piperizinyl, pyrrolidinyl, imidazolindinyl, imidazolinyl, indolinyl, isoindolinyl, quinuclidinyl, morpholinyl, isochromanyl, chromanyl, pyrazolidinyl and pyrazolinyl groups.

Typical heterocycloalkyl groups include any of the above-mentioned $C_{1-10}$ alkyl groups substituted by any of the above-mentioned heterocyclic groups.

Typical heteroaryl groups include any one of the following which may be optionally substituted with one or more alkyl, halo, or hydroxy groups: thienyl, benzo[b]thienyl, naphtho[2,3-b]thienyl, thianthrenyl, furyl, pyranyl, isobenzofuranyl, chromenyl, xanthenyl, phenoxanthiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, 5aH-carbozolyl, carbozolyl, β-carbolinyl, phenanthridinyl, acrindinyl, perimidinyl, phenanthrolinyl, phenazinyl, isothiazolyl, phenothiazinyl, isoxazolyl, furazanyl, phenoxazinyl, 1,4-dihydroquinoxaline-2,3-dione, 7-aminoisocoumarin, pyrido[1,2-a]pyrimidin-4-one, 1,2-benzoisoxazol-3-yl, 4-nitrobenzofurazan, benzimidazolyl, 2-oxindolyl and 2-oxobenzimidazolyl. Where the heteroaryl group contains a nitrogen atom in a ring, such nitrogen atom may be in the form of an N-oxide, e.g. a pyridyl N-oxide, pyrazinyl N-oxide, pyrimidinyl N-oxide and the like.

Typical heteroarylalkyl groups include any of the above-mentioned $C_{1-10}$ alkyl groups substituted by any of the above-mentioned heteroaryl groups.

Typical heteroarylalkenyl groups include any of the above-mentioned $C_{2-4}$ alkenyl groups substituted by any of the above-mentioned heteroaryl groups.

Typical heteroarylalkynyl groups include any of the above-mentioned $C_{2-4}$ alkynyl groups substituted by any of the above-mentioned heteroaryl groups.

Typical amino groups include —$NH_2$, —$NHR_{14}$, and —$NR_{14}R_{15}$, wherein $R_{14}$ and $R_{15}$ are $C_{1-10}$ alkyl groups as defined above.

Typical carbonylamido groups are carbonyl groups substituted by —$NH_2$, —$NHR_{14}$, and —$NR_{14}R_{15}$ groups as defined above.

When the group is an amidino or guanidino group, any one of the nitrogen atoms may be substituted independently by hydrogen, alkyl, or aryl groups.

Optional substituents on the aryl, aralkyl, aryloxy, arylthioxy, aroyl, heterocyclic, heterocycloxy, heteroaryl, heteroaryloxy, cycloalkyl, and cycloalkoxy groups listed above include any one of the typical halo, haloalkyl, aryl, fused aryl, heterocyclic, heteroaryl, alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, nitro, amino, cyano, acylamido, hydroxy, thiol, acyloxy, azido, alkoxy, carboxy, carbonylamido, and alkylthiol groups mentioned above.

Exemplary preferred compounds of formula I include, without limitation:

7,8-methylenedioxy-1-phenyl-3,5-dihydro-2,3-benzodiazepin-4(4H)-one, 7,8-ethylenedioxy-1-phenyl-3,5-dihydro-2,3-benzodiazepin-4(4H)-one, 1-phenylcyclopenta[h]-3,5-dihydro-2,3-benzodiazepin-4(4H)-one, 3-methylaminocarbonyl-7,8-methylenedioxy-1-phenyl-3,5-dihydro-2,3-benzodiazepin-4(4H)-one, 1-(4-aminophenyl)-7,8-methylenedioxy-3,5-dihydro-2,3-benzodiazepin-4(4H)-one, 1-(4-aminophenyl)-6-chloro-7,8-methylenedioxy-3,5-dihydro-2,3-benzodiazepin-4(4H)-one, 1-(4-aminophenyl)-9-chloro-7,8-methylenedioxy-3,5-dihydro-2,3-benzodiazepin-4(4H)-one, 1-(4-isopropylaminophenyl)-7,8-methylenedioxy-3,5-dihydro-2,3-benzodiazepin-4(4H)-one, 7,8-methylenedioxy-1-(4-methylphenyl)-3,5-dihydro-2,3-benzodiazepin-4(4H)-one, 7,8-methylenedioxy-1-(4-methoxyphenyl)-3,5-dihydro-2,3-benzodiazepin-4(4H)-one, 1-(3-aminophenyl)-7,8-methylenedioxy-3,5-dihydro-2,3-benzodiazepin-4(4H)-one, 1-(4-hydroxyphenyl)-7,8-methylenedioxy-3,5-dihydro-2,3-benzodiazepin-4(4H)-one, 1-(4-amino-3-methylphenyl)-7,8-methylenedioxy-3,5-dihydro-2,3-benzodiazepin-4(4H)-one, 1-(4-amino-3-chlorophenyl)-7,8-methylenedioxy-3,5-dihydro-2,3-benzodiazepin-4(4H)-one, 1-(4-aminophenyl)-5-methyl-7,8-methylenedioxy-3,5-dihydro-2,3-benzodiazepin-4(4H)-one, 1-(4-amino-2-chlorophenyl)-7,8-methylenedioxy-3,5-dihydro-2,3-benzodiazepin-4(4H)-one, 7,8-methylenedioxy-1-(3,4-methylenedioxyphenyl)-3,5-dihydro-2,3-benzodiazepin-4(4H)-one, 7,8-methylenedioxy-1-(3,4-methylenedioxyphenyl)-5-methyl-3,5-dihydro-2,3-benzodiazepin-4(4H)-one, 1-(4-acetamidophenyl)-7,8-methylenedioxy-5-methyl-3,5-dihydro-2,3-benzodiazepin-4(4H)-one, 1-(4-azidophenyl)-7,8-methylenedioxy-3,5-dihydro-2,3-benzodiazepin-4(4H)-one, 1-(4-methylaminophenyl)-7,8-methylenedioxy-3,5-dihydro-2,3-benzodiazepin-4(4H)-one, 3-cycloheptyl-7,8-methylenedioxy-1-phenyl-3,5-dihydro-2,3-benzodiazepin-4(4H)-one, 3-(3-hexyl)-7,8-methylenedioxy-1-phenyl-3,5-dihydro-2,3-benzodiazepin-4(4H)-one, 7,8-methylenedioxy-3-(2-pentyl)-1-phenyl-3,5-dihydro-2,3-benzodiazepin-4(4H)-one, 3-cyclohexyl-7,8-methylenedioxy-1-phenyl-3,5-dihydro-2,3-benzodiazepin-4(4H)-one, 3-cyclopentyl-7,8-methylenedioxy-1-phenyl-3,5-dihydro-2,3-benzodiazepin-4(4H)-one, 3-isopropyl-7,8-methylenedioxy-1-phenyl-3,5-dihydro-2,3-benzodiazepin-4(4H)-one, 3-(2-butyl)-7,8-methylenedioxy-1-phenyl-3,5-dihydro-2,3-benzodiazepin-4(4H)-one, and 7,8-methylenedioxy-3-(3-pentyl)-1-phenyl-3,5-dihydro-2,3-benzodiazepin-4(4H)-one.

Certain of the compounds of the present invention may exist as optical isomers and the invention includes both the racemic mixtures of such optical isomers as well as the individual entantiomers that may be separated according to methods that are well known to those of ordinary skill in the art.

Examples of pharmaceuticallly acceptable addition salts include inorganic and organic acid addition salts such as hydrochloride, hydrobromide, phosphate, sulphate, citrate, lactate, tartrate, maleate, fumarate, mandelate and oxalate.

Examples of prodrugs include ester or amide of formula I with $R_3$ as hydroxyalkyl or aminoalkyl, by reacting such compounds with anhydride such as succinic anhydride.

The invention is also directed to a method for treating disorders responsive to the blockade of AMPA receptors in animals suffering thereof. Particular prefered embodiments of the substituted 2,3-benzodiazepin-4-ones for use in method of this invention are represented by previously defined Formula I, with $R_3$ preferred to be hydrogen, COR, $CO_2R$ and $CONR_xR_y$, wherein R, $R_x$ and $R_y$ are as defined previously with respect to Formula I. Exemplary preferred compounds that may be employed in this method of invention include, without limitation:

7,8-methylenedioxy-1-phenyl-3,5-dihydro-2,3-benzodiazepin-4(4H)-one, 7,8-ethylenedioxy-1-phenyl-3,5-dihydro-2,3-benzodiazepin-4(4H)-one, 1-phenylcyclopenta[h]-3,5-dihydro-2,3-benzodiazepin-4(4H)-one, 3-methylaminocarbonyl-7,8-methylenedioxy-1-phenyl-3,5-dihydro-2,3-benzodiazepin-4(4H)-one,
1-(4-aminophenyl)-7,8-methylenedioxy-3,5-dihydro-2,3-benzodiazepin-4(4H)-one,
1-(4-aminophenyl)-6-chloro-7,8-methylenedioxy-3,5-dihydro-2,3-benzodiazepin-4(4H)-one,
1-(4-aminophenyl)-9-chloro-7,8-methylenedioxy-3,5-dihydro-2,3-benzodiazepin-4(4H)-one,
7,8-methylenedioxy-1-(4-methylphenyl)-3,5-dihydro-2,3-benzodiazepin-4(4H)-one,
7,8-methylenedioxy-1-(4-methoxyphenyl)-3,5-dihydro-2,3-benzodiazepin-4(4H)-one,
1-(3-aminophenyl)-7,8-methylenedioxy-3,5-dihydro-2,3-benzodiazepin-4(4H)-one,
1-(4-hydroxyphenyl)-7,8-methylenedioxy-3,5-dihydro-2,3-benzodiazepin-4(4H)-one,
1-(4-amino-3-methylphenyl)-7,8-methylenedioxy-3,5-dihydro-2,3-benzodiazepin-4(4H)-one,
1-(4-amino-3-chlorophenyl)-7,8-methylenedioxy-3,5-dihydro-2,3-benzodiazepin-4(4H)-one,
1-(4-aminophenyl)-5-methyl-7,8-methylenedioxy-3,5-dihydro-2,3-benzodiazepin-4(4H)-one,
1-(4-amino-2-chlorophenyl)-7,8-methylenedioxy-3,5-dihydro-2,3-benzodiazepin-4(4H)-one,
7,8-methylenedioxy-1-(3,4-methylenedioxyphenyl)-3,5-dihydro-2,3-benzodiazepin-4(4H)-one,
7,8-methylenedioxy-1-(3,4-methylenedioxyphenyl)-5-methyl-3,5-dihydro-2,3-benzodiazepin-4(4H)-one,
1-(4-acetamidophenyl)-7,8-methylenedioxy-5-methyl-3,5-dihydro-2,3-benzodiazepin-4(4H)-one,
1-(4-azidophenyl)-7,8-methylenedioxy-3,5-dihydro-2,3-benzodiazepin-4(4H)-one, and
1-(4-methylaminophenyl)-7,8-methylenedioxy-3,5-dihydro-2,3-benzodiazepin-4(4H)-one.

The invention is also directed to a method for treating disorders responsive to the positive modulation of AMPA receptors in animals suffering thereof. Particular preferred embodiments of the substituted 2,3-benzodiazepin-4-ones for use in method of this invention are represented by previously defined Formula I, with $R_3$ preferred to be $C_{3-10}$ alkyl, arylalkyl, heteroarylalkyl, or carbocyclic group, carbocycloalkyl group, heterocycle group and heterocycloalkyl group. Exemplary preferred compounds that may be employed in this method of invention include, without limitation:

3-cycloheptyl-7,8-methylenedioxy-1-phenyl-3,5-dihydro-2,3-benzodiazepin-4(4H)-one,
3-(3-hexyl)-7,8-methylenedioxy-1-phenyl-3,5-dihydro-2,3-benzodiazepin-4(4H)-one,
7,8-methylenedioxy-3-(2-pentyl)-1-phenyl-3,5-dihydro-2,3-benzodiazepin-4(4H)-one,
3-cyclohexyl-7,8-methylenedioxy-1-phenyl-3,5-dihydro-2,3-benzodiazepin-4(4H)-one,
3-cyclopentyl-7,8-methylenedioxy-1-phenyl-3,5-dihydro-2,3-benzodiazepin-4(4H)-one,
3-isopropyl-7,8-methylenedioxy-1-phenyl-3,5-dihydro-2,3-benzodiazepin-4(4H)-one,
3-(2-butyl)-7,8-methylenedioxy-1-phenyl-3,5-dihydro-2,3-benzodiazepin-4(4H)-one, and
7,8-methylenedioxy-3-(3-pentyl)-1-phenyl-3,5-dihydro-2,3-benzodiazepin-4(4H)-one.

The compounds of this invention may be prepared using methods well known to those skilled in the art, or by the novel methods of this invention. Exemplary reactions are illustrated in Schemes I and II. The starting materials employed in Scheme I and II are readily available or can be prepared by known methods.

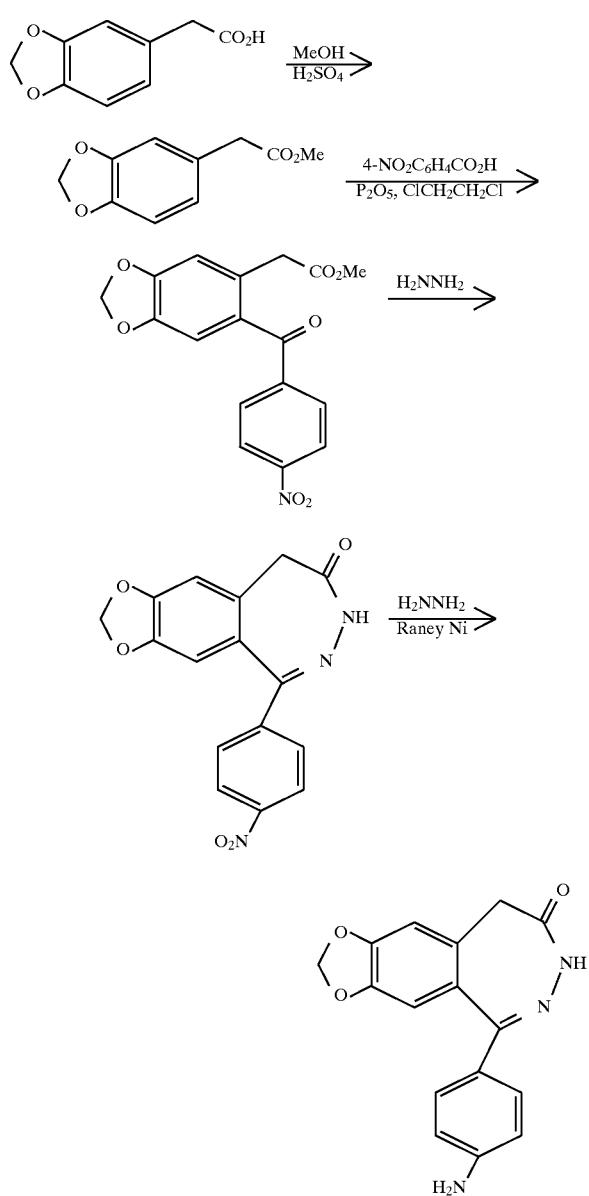

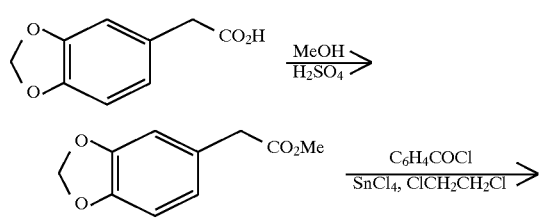

-continued
Scheme II

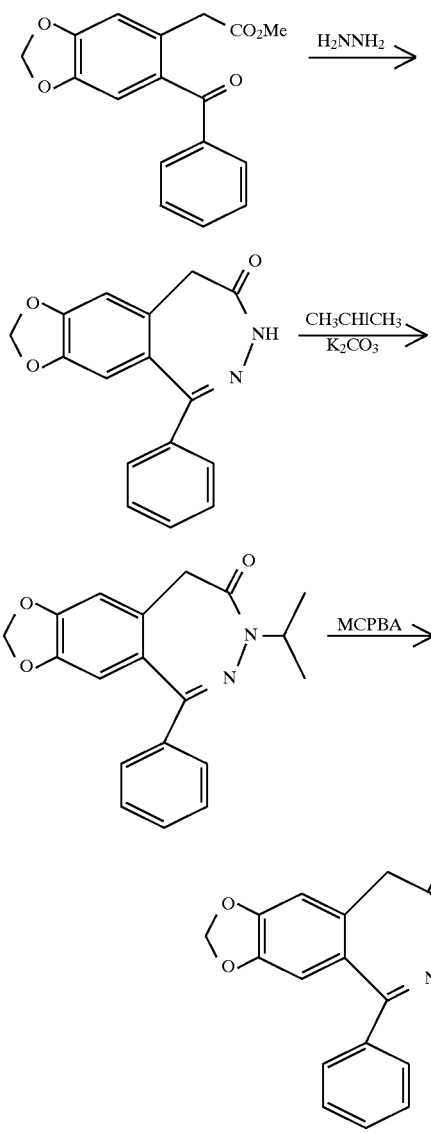

The novel substituted 2,3-benzodiazepin-4-ones were assessed by electrophysiological assays in Xenopus oocytes expressing rat whole brain poly(A)+RNA (see Keana et al, *J. Med. Chem.* 38. 4367–4379 (1995)) or in cultured rat cortical neurons (see Woodward et. al. *Mol. Pharmacol.* 47: 568–581 (1995)) for AMPA receptor activity. Compounds which are useful for treating or preventing the adverse consequences of stroke, hypoglycemia, neurodegenerative disorders, anxiety, epilepsy or psychosis, or which induce analgesia, will inhibit the currents across the membranes of the oocyte expressing AMPA receptors. However, if the compound potentiates currents across the oocyte membrane, then the compound is expected to be useful in enhancing cognition or treating schizophrenia or neurodegenerative diseases such as Parkinson's Disease.

The compounds of the present invention are active in treating, preventing or ameliorating neuronal loss, neurodegenerative diseases, chronic pain, are active as anticonvulsants and inducing anesthesia. They are also useful for treating or ameliorating epilepsy and psychosis.

Neurodegenerative diseases which may be treated or ameliorated with the compounds of the present invention include those selected from the group consisting of Alzheimer's disease, amyotrophic lateral sclerosis, Huntington's disease, Parkinson's disease and Down's syndrome.

The compounds of the present invention find particular utility in the treatment of global and focal ischemia or prevention of neuronal loss associated with multiple strokes which give rise to dementia. After a patient has a cardiac arrest, the compounds of the present invention may be administered to ameliorate the ischemia related neuronal damage that may occur from cardiac arrest and other causes of global ischemia.

The compounds of the invention find particular utility in treating, preventing or ameliorating the adverse neurological consequences of surgery. For example, coronary bypass surgery requires the use of heart-lung machines which tend to introduce air bubbles into the circulatory system which may lodge in the brain. The presence of such air bubbles robs neuronal tissue of oxygen, resulting in anoxia and ischemia. Pre- or post- surgical administration of the compounds of the present invention will treat or prevent the resulting ischemia. In a preferred embodiment, the compounds of the invention are administered to patients undergoing cardiopulmonary bypass surgery or carotid endarterectomy surgery.

The compounds of the present invention also find utility in treating, preventing or ameliorating chronic pain. Such chronic pain may be the result of surgery, trauma, headache, arthritis, pain from terminal cancer or degenerative diseases. The compounds of the present invention also find particular utility in the treatment of phantom pain that results from amputation of an extremity. In addition to treatment of pain, the compounds of the invention are also expected to be useful in treating muscle spasm and inducing anesthesia, either general or local anesthesia, for example, during surgery.

The compounds of the present invention may be tested for in vivo anticonvulsant activity after iv or ip injection using a number of anticonvulsant tests in mice (audiogenic seizure model in DBA-2 mice, pentylenetetrazol-induced seizures in mice, maximum electroshock seizure test (MES)).

The compounds may be tested for their neuroprotective activity after focal and global ischemia produced in rats or gerbils according to the procedures described in Buchan et. al. (*Stroke*, Suppl. 148–152 (1993)) and Sheardown et. al. (*Eur. J. Pharmacol.* 236: 347–353 (1993)) and Graham et. al. (*J. Pharmacol. Exp. Therap.* 276: 1–4 (1996)).

The compounds may be tested for their neuroprotective activity after traumatic spinal cord injury according to the procedures described in Wrathall et. al. (*Exp. Neurology* 137. 119–126 (1996)) and Iwasaki et. al. (*J. Neuro Sci.* 134:21–25 (1995)).

The compounds may also be tested in drug discrimination tests in rats trained to discriminate PCP from saline. It is expected that most of the compounds of the present invention will not generalize to PCP at any doses. In addition, it is also expected that none of the compounds will produce a behavioral excitation in locomotor activity tests in the mouse.

Elevated levels of glutamate have been associated with glaucoma. In addition, it has been disclosed that glaucoma management, particularly protection of retinal ganglion cells, can be achieved by administering to a patient a compound capable of reducing glutamate-induced excitotoxicity in a concentration effective to reduce the excitotoxicity. See WO94/13275. Thus, the compounds of the present invention, which are expected to cross the blood-retina barrier, are also expected to be useful in the treatment or amelioration of glaucoma. Preferably, the invention is directed to the treatment of patients which have primary open-angle glaucoma, chronic closed-angle glaucoma, pseudoexfoliation, or other types of glaucoma or ocular hypertension. Preferably, the compound is administered over an extended period (e.g. at least six months and preferably at least one year), regardless of the changes in the patient's intraocular pressure over the period of administration.

AMPA receptor antagonists are also useful in treating CMV retinitis, particularly in combination with antiviral agents. CMV affects the ganglion cell layer, which may result in high concentrations of glutamate. Thus, glutamate receptor antagonists could block retinitis by blocking the toxicity of high levels of glutamate.

The compounds of the present invention show potent activity in vivo after intraperitoneal injection suggesting that these compounds can penetrate the blood/brain barrier and are systemically bioavailable.

Thus, the present invention is directed to substituted 2,3-benzodiazepin-4-ones having preferred binding to AMPA receptors. According to the present invention, those compounds having preferred binding to AMPA receptors exhibit an $IC_{50}$ of about 100 $\mu$M or less in the electrophysiological assay. Preferably, the compounds of the present invention exhibit an $IC_{50}$ of 10 $\mu$M or less. Most preferably, the compounds of the present invention exhibit an $IC_{50}$ of about 1.0 $\mu$M or less.

The efficacy of the AMPA antagonists to inhibit glutamate neurotoxicity in rat brain cortex neuron cell culture system may be determined according to Choi, W., *J. Neuroscience* 7: 357 (1987).

The anticonvulsant activity of the AMPA antagonists may be evaluated in the Maximal Electroshock-induced Seizure (MES) test. Seizures are induced by application of current (50 mA, 60 pulses/sec, 0.8 sec pulse width, 1 sec duration, .c.) through saline-coated corneal electrodes using a Ugo Basile ECT device (Model 7801). Mice are restrained by gripping the loose skin on their dorsal surface, electrodes were held lightly against the two cornea, then current was applied and mice were observed for a period of up to 30 sec for the occurrence of a tonic hindlimb extensor response. A tonic seizure is defined as a hindlimb extension in excess of 90 degrees from the plane of the body. Results are treated in a quintal manner.

The anticonvulsant efficacy of the AMPA antagonists may also be assessed in the pentylenetetrazol (PTZ)-induced seizure test according to WO94/00124.

It is known that AMPA receptors are critically involved in the development of persistent pain following nerve and tissue injury. The effects of the AMPA receptor antagonists of the present invention on pain may be evaluated according to WO94/00124.

The anxiolytic activity of any particular compound described herein may be determined by use of any of the recognized animal models for anxiety. A preferred model is described by Jones, B. J. et al., Br. *J. Pharmacol.* 93: 985–993 (1988).

Compositions within the scope of this invention include all compositions wherein the compounds of the present invention are contained in an amount which is effective to achieve its intended purpose. While individual needs vary, determination of optimal ranges of effective amounts of each component is with the skill of the art. Typically, the compounds may be administered to mammals, e.g. humans, orally at a dose of 0.0025 to 50 mg/kg, or an equivalent amount of the pharmaceutically acceptable salt thereof, per day of the body weight of the mammal being treated for psychosis or anxiety disorders, e.g., generalized anxiety disorder, phobic disorders, obsessional compulsive disorder, panic disorder, and post traumatic stress disorders. Preferably, about 0.01 to about 10 mg/kg is orally administered to treat or prevent such disorders. For intramuscular injection, the dose is generally about one-half of the oral dose. For example, for treatment or prevention of anxiety, a suitable intramuscular dose would be about 0.0025 to about 15 mg/kg, and most preferably, from about 0.01 to about 10 mg/kg.

In the method of treatment or prevention of neuronal loss in global and focal ischemia, brain and spinal cord trauma, hypoxia, hypoglycemia, status epilepsy and surgery, the compound can be administered by intravenous injection at a dose of 0.025 to 10 mg/kg. For the treatment of AIDS associated neuronal damage, Alzheimer's disease, amyotrophic lateral sclerosis, Huntington's disease and Down's Syndrome, or in a method of treating a disease in which the pathophysiology of the disorder involves hyperactivity of the excitatory amino acids (e.g. convulsions) or AMPA receptor-ion channel related neurotoxicity, the pharmaceutical compositions of the invention may comprise the compounds of the present invention at a unit dose level of about 0.01 to about 50 mg/kg of body weight, or an equivalent amount of the pharmaceutically acceptable salt thereof, on a regimen of 1–4 times per day. When used to treat chronic pain, to induce anesthesia, or to treat or prevent glaucoma, migraine headache, muscle spasm or urinary incontinence, the compounds of the invention may be administered at a unit dosage level of from about 0.01 to about 50 mg/kg of body weight, or an equivalent amount of the pharmaceutically acceptable salt thereof, on a regimen of 1–4 times per day. Of course, it is understood that the exact treatment level will depend upon the case history of the animal, e.g., human being, that is treated. The precise treatment level can be determined by one of ordinary skill in the art without undue experimentation.

The unit oral dose may comprise from about 0.01 to about 50 mg, preferably about 0.1 to about 10 mg of the compound. The unit dose may be administered one or more times daily as one or more tablets each containing from about 0.1 to about 10, conveniently about 0.25 to 50 mg of the compound or its solvates.

In addition to administering the compound as a raw chemical, the compounds of the invention may be administered as part of a pharmaceutical preparation containing suitable pharmaceutically acceptable carriers comprising excipients and auxiliaries which facilitate processing of the compounds into preparations which can be used pharmaceutically. Preferably, the preparations, particularly those preparations which can be administered orally and which can be used for the preferred type of administration, such as tablets, dragees, and capsules, and also preparations which can be administered rectally, such as suppositories, as well as suitable solutions for administration by injection or orally, contain from about 0.01 to 99 percent, preferably from about 0.25 to 75 percent of active compound(s), together with the excipient.

Also included within the scope of the present invention are the non-toxic pharmaceutically acceptable salts of the compounds of the present invention. Acid addition salts are formed by mixing a solution of the particular AMPA antagonist or positive modulator of the present invention with a solution of a pharmaceutically acceptable non-toxic acid such as hydrochloric acid, fumaric acid, maleic acid, succinic acid, acetic acid, dichloroacetic acid, citric acid, tartaric acid, carbonic acid, phosphoric acid, oxalic acid, and the like. Basic salts are formed by mixing a solution of the particular AMPA antagonist or positive modulator of the present invention with a solution of a pharmaceutically acceptable non-toxic base such as sodium hydroxide, potassium hydroxide, choline hydroxide, sodium carbonate and the like.

The pharmaceutical compositions of the invention may be administered to any animal which may experience the beneficial effects of the compounds of the invention. Foremost among such animals are mammals, e.g., humans, although the invention is not intended to be so limited.

The pharmaceutical compositions of the present invention may be administered by any means that achieve their intended purpose. For example, administration may be by parenteral, subcutaneous, intravenous, intramuscular, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropymethylcellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions may contain substances which increase the viscosity of the suspension include, for example, sodium carboxymethyl cellulose, sorbitol, and/or dextran. Optionally, the suspension may also contain stabilizers.

The characterization of non-competitive AMPA receptors antagonists in vitro has been difficult because of the lack of selective drug ligands. Thus, the AMPA ligands of the present invention may be used to characterize the AMPA receptors and their distribution. Particularly preferred AMPA antagonists and positive modulator of the present invention which may be used for this purpose are isotopically radiolabelled derivatives, e.g. where one or more of the atoms are replaced with $^3$H, $^{11}$C, $^{14}$C or $^{18}$F. Alternatively, a fluorescent group Y may be employed. Examples of such groups include 4-nitrobenzofurazan.

The following examples are illustrative, but not limiting, of the method and compositions of the present invention. Other suitable modifications and adaptations of the variety of conditions and parameters normally encountered in clinical therapy and which are obvious to those skilled in the art are within the spirit and scope of the invention.

EXAMPLE 1

Methyl 3,4-methylenedioxyphenylacetate

To a solution of 3,4-methylenedioxyphenylacetic acid (4.2 g, 23 mmol) in methanol (50 mL) was added concentrated sulfuric acid (1.5 mL). The mixture was refluxed for 48 h, cooled to room temperature, and neutralized with saturated NaHCO$_3$. The methanol was removed in vacuo. The residue was extracted with 1:1 hexane/EtOAc (2×100 mL). The combined organic phase was washed with water, saturated NaHCO$_3$, and brine, and dried over Na$_2$SO$_4$. The solvent was removed in vacuo to yield the title compound as an oil (3.9 g, 86%). $^1$H NMR (CDCl$_3$) 6.78–6.72 (m, 3H), 5.95 (s, 2H), 3.69 (s, 3H), 3.54 (s, 2H).

EXAMPLE 2

Methyl 2-Benzoyl-4,5-methylenedioxyphenylacetate

To a solution of methyl 3,4-methylenedioxyphenylacetate (150 mg, 0.77 mmol) in CH$_2$Cl$_2$ (5 mL) was added SnCl$_4$ (1.0M solution in CH$_2$Cl$_2$; 1.5 mL, 1.5 mmol) at 0° C. Then benzoyl chloride (130 μL, 1.1 mmol) was added. The reaction mixture was allowed to warm slowly to room temperature. After 24 h, the mixture was added to a saturated NaHCO$_3$ solution (30 mL), diluted with 1:1 hexane/EtOAc (60 mL), washed with water and brine, and dried over Na$_2$SO$_4$. The solvent was removed in vacuo and the resulting residue was separated by chromatography on silica gel (4:1 hexane/EtOAc) to yield the title compound (110 mg, 48%). $^1$H NMR (CDCl$_3$) 7.78–7.45 (m, 5H), 6.88 (s, 1H), 6.84 (s, 1H), 6.04 (s, 2H), 3.80 (s, 2H), 3.61 (s, 3H).

EXAMPLE 3

Methyl 2-(4-Methylbenzoyl)-4,5-methylenedioxyphenylacetate

The title compound was prepared from methyl 3,4-methylenedioxyphenylacetate (319 mg, 1.64 mmol) in CH$_2$Cl$_2$ (5 mL), SnCl$_4$ (1.0M solution in CH$_2$Cl$_2$; 3.5 mL mmol) and 4-toluoyl chloride (260 µL, 1.97 mmol) as an oily solid (90 mg, 18%). $^1$H NMR (CDCl$_3$) 7.69 (d, 2H, J=8.0), 7.24 (d, 2H, J=8.0), 6.88 (s, 1H), 6.83 (s, (s, 2H), 3.78 (s, 2H), 3.60 (s, 3H), 2.43 (s, 3H).

EXAMPLE 4

Methyl 2-(4-Methoxybenzoyl)-4,5-methylenedioxyphenylacetate

The title compound was prepared from methyl 3,4-methylenedioxyphenylacetate (244 mg, 1.26 mmol) in CH$_2$Cl$_2$ (5 mL), SnCl$_4$ (1.0M solution in CH$_2$Cl$_2$; 2.5 mL 2.5 mmol) and 4-anisoyl chloride (220 µL, 1.62 mmol) as a white solid (110 mg, 27%). $^1$H NMR (CDCl$_3$) 7.78 (d, 2H, J=8.6), 6.93 (d, 2H, J=8.6), 6.86 (s, 1H), 6.83 (s, 1H), 6.03 (s, 2H), 3.88 (s, 3H), 3.75 (s, 2H), 3.59 (s, 3H).

EXAMPLE 5

Methyl 2-(4-Fluorobenzoyl)-4,5-methylenedioxyphenylacetate

The title compound was prepared from methyl 3,4-methylenedioxyphenylacetate (340 mg, 1.75 mmol) in CH$_2$Cl$_2$ (8 mL), SnCl$_4$ (1.0M solution in CH$_2$Cl$_2$; 3.5 mL, 3.5 mmol) and 4-fluorobenzoyl chloride (270 µL, 2.28 mmol) as a solid (350 mg, 63%). $^1$H NMR (CDCl$_3$) 7.81 (m, 2H), 7.13 (m, 2H), 6.85 (s, 1H), 6.84 (s, 1H), 6.04 (s, 2H), 3.79 (s, 2H), 3.61 (s, 3H).

EXAMPLE 6

Methyl 2-(2-Furoyl)-4,5-methylenedioxyphenylacetate

The title compound was prepared from methyl 3,4-methylenedioxyphenylacetate (336 mg, 1.73 mmol) in CH$_2$Cl$_2$ (10 mL), SnCl$_4$ (1.0M solution in CH$_2$Cl$_2$; 2.8 mL, 2.8 mmol) and 2-furoyl chloride (200 µL, 1.92 mmol) as a solid (120 mg, 52% yield at 46% conversion). $^1$H NMR (CDCl$_3$) 7.68 (brs, 1H), 7.17 (s, 1H), 7.11 (d, 1H, J=3.5), 6.83 (s, 1H), 6.57 (m, 1H), 6.06 (s, 2H), 3.78 (s, 2H), 3.64 (s, 3H).

EXAMPLE 7

Methyl 4,5-Methylenedioxy-2-(4-nitrobenzoyl) phenylacetate

To a solution of methyl 3,4-methylenedioxyphenylacetate (5.4 g, 28 mmol) in ClCH$_2$CH$_2$Cl (100 mL) was added 4-nitrobenzoic acid (7.2 g, 43 mmol) and P$_2$O$_5$ (18 g) at room temperature under argon. The mixture was refluxed for 28 h, cooled to room temperature, then cold water was added slowly. The resulting mixture was carefully neutralized with solid K$_2$CO$_3$, and extracted with 1:1 hexane/EtOAc (2×300 mL). The combined extracts were washed with water and brine, and dried over Na$_2$SO$_4$. The solvent was removed in vacuo and the resulting residue was separated by chromatography (3:1 hexane/EtOAc) to afford the title compound as a yellow solid (4.7 g, 14 mmol, 50%). $^1$H NMR (CDCl$_3$) 8.32 (d, 2H, J=8.5), 7.92 (d, 2H, J=8.5), 6.85 (s, 1H), 6.81 (s, 1H), 6.07 (s, 2H), 3.88 (s, 2H), 3.63 (s, 3H).

EXAMPLE 8

7,8-Methylenedioxy-1-phenyl-3,5-dihydro-2,3-benzodiazepin-4(4H)-one

A solution of methyl 2-benzoyl-4,5-methylenedioxyphenylacetate (110 mg, 0.37 mmol) and hydrazine hydrate (30 µL, 0.53 mmol) in ethanol (15 mL) was refluxed for 5 days. The solvent was removed in vacuo and the resulting residue was separated by chromatography to yield the title compound (30 mg, 0.11 mmol, 29%), mp, 182°–184° C. $^1$H NMR (CDCl$_3$) 8.59 (s, 1H), 7.60–7.41 (m, 5H), 6.83 (s, 1H), 6.63 (s, 1H), 6.03 (s, 2H), 3.46 (s, 2H). Anal. Calcd. for C$_{16}$H$_{12}$N$_2$O$_3$.0.25H$_2$O: C, 67.48; H, 4.42; N, 9.84. Found C, 67.25; H, 4.21; N, 9.88.

EXAMPLE 9

7,8-Methylenedioxy-1-(4-methylphenyl)-3,5-dihydro-2,3-benzodiazepin-4(4H)-one

The title compound was prepared from methyl 4,5-methylenedioxy-2-(4-methylbenzoyl)phenylacetate (90 mg, 0.29 mmol), hydrazine hydrate (50 µL, 0.88 mmol) and acetic acid (40 µL) in ethanol (10 mL), mp: 222°–224° C. $^1$H NMR (CDCl$_3$) 8.36 (s, 1H), 7.48 (d, 2H, J=8.0), 7.23 (d, 2H, J=8.0), 6.82 (s, 1H), 6.64 (s, 1H), 6.02 (s, 2H), 3.45 (s, 2H), 2.41 (s, 3H). Anal. Calcd. for C$_{17}$H$_{14}$N$_2$O$_3$: C, 69.38; H, 4.79; N, 9.52. Found: C, 69.14; H, 4.80; N, 9.30.

EXAMPLE 10

1-(4-Methoxyphenyl)-7,8-methylenedioxy-3,5-dihydro-2,3-benzodiazepin-4(4H)-one

The title compound was prepared from methyl 4,5-methylenedioxy-2-(4-methoxybenzoyl)phenylacetate (102 mg, 0.31 mmol) and hydrazine hydrate (30 µL, 0.53 mmol) in 1-propanol (8 mL), mp: 194°–196° C. $^1$H NMR (CDCl$_3$) 8.48 (s, 1H), 7.55 (d, 2H, J=8.8), 6.94 (d, 2H, J=8.8), 6.83 (s, 1H), 6.66 (s, 1H), 6.03 (s, 2H), 3.86 (s, 3H), 3.44 (s, 2H). Anal. calcd. for C$_{17}$H$_{14}$N$_2$O$_4$: C, 65.80; H, 4.55; N, 9.03. Found: C, 65.56; H, 4.57; N, 8.72.

EXAMPLE 11

1-(4-Fluorophenyl)-7,8-methylenedioxy-3,5-dihydro-2,3-benzodiazepin-4(4H)-one

The title compound was prepared from methyl 2-(4-fluorobenzoyl)-4,5-methylenedioxyphenylacetate (350 mg, 1.11 mmol), hydrazine hydrate (180 µL, 3.18 mmol), and acetic acid (50 µL) in ethanol (10 mL), mp: 205°–207° C. 1H NMR (CDCl$_3$) 8.45 (s, 1H), 7.59 (dd, 2H, J=8.5, J=5.5), 7.11 (dd, 2H, J=8.5, J=8.5), 6.83 (s, 1H), 6.61 (s, 1H), 6.04 (s, 2H), 3.45 (s, 2H). Anal. calcd. for C$_{16}$H$_{11}$FN$_2$O$_3$.0.125 H$_2$O: C, 63.94; H, 3.77; N, 9.32. Found: C, 63.83; H, 3.58; N, 9.03.

EXAMPLE 12

1-(2-Furyl)-7,8-methylenedioxy-3,5-dihydro-2,3-benzodiazepin-4(4H)-one

The title compound was prepared from methyl 2-(2-furoyl)-4,5-methylenedioxyphenylacetate (120 mg, 0.42 mmol), hydrazine hydrate (70 μL, 1.2 mmol), and acetic acid (50 μL) in ethanol (20 mL) as a light yellow solid (37 mg, 33%), mp: 234°–236° C. $^1$H NMR (CDCl$_3$) 8.50 (s, 1H), 7.60 (m, 1H), 7.00 (s, 1H), 6.82 (s, 1H), 6.71 (m, 1H), 6.54 (m, 1H), 6.06 (s, 2H), 3.44 (s, 2H). Anal. Calcd. for C$_{14}$H$_{10}$N$_2$O$_4$: C, 62.22; H, 3.73; N, 10.37. Found: C, 62.07; H, 3.63; N, 10.11.

EXAMPLE 13

7,8-Methylenedioxy-1-(4-nitrophenyl)-3,5-dihydro-2,3-benzodiazepin-4(4H)-one A solution of methyl 4,5-methylenedioxy-2-(4-nitrobenzoyl)phenylacetate (90 mg, 0.26 mmol), hydrazine hydrate (50 μL, 0.88 mmol), and acetic acid (40 μL) in ethanol (15 mL) was refluxed for 4 days. A yellow solid precipitated out from the solution. After cooling, the solvent was removed via pipette and the solid was washed with EtOAc (twice) and hexane, dried in vacuo to provide the title compound (40 mg, 47%), mp: 293°–295° C. $^1$H NMR (DMSO-d$_6$) 11.2 (s, 1H), 8.31(d, 2H, J=8.8), 7.79 (d, 2H, J=8.8), 7.13 (s, 1H), 6.65 (s, 1H), 6.12 (s, 2H), 3.45 (s, 2H). Anal. Calcd. for C$_{16}$H$_{11}$N$_3$O$_5$: C, 59.08; H, 3.41; N, 12.92. Found: C, 59.05; H, 3.43; N, 2.83.

EXAMPLE 14

1-(4-Aminophenyl)-7,8-methylenedioxy-3,5-dihydro-2,3-benzodiazepin-4(4H)-one To a suspension of 7,8-methylenedioxy-1-(4-nitrophenyl)-3,5-dihydro-2,3-benzodiazepin-4(4H)-one (167 mg, 0.51 mmol) in ethanol (8 mL) was added Raney Ni (430 mg), hydrazine hydrate (200 μL, 3.5 mmol) and 2N HCl (150 μL, 0.3 mmol). The mixture was stirred at room temperature for 17 h. The solid Ni was filtered out. The filtrate was concentrated in vacuo and the resulting residue was separated by chromatography (1:4 hexane/EtOAc) to afford the title compound as a yellow solid (110 mg, 0.37 mmol, 73%), mp: 242°–244° C. $^1$H NMR (CDCl$_3$) 8.32 (s, 1H), 7.41 (d, 2H, J=8.5), 6.81 (s, 1H), 6.70 (s, 1H), 6.68 (d, 2H, J=8.5), 6.02 (s, 2H), 3.94 (brs, 2H), 3.42 (s, 2H). Anal. Calcd. for C$_{16}$H$_{13}$N$_3$O$_3$·0.25H$_2$O: C, 64.10; H, 4.54; N, 14.02. Found C, 64.32; H, 4.37; N, 13.48.

EXAMPLE 15

7,8-Methylenedioxy-3-methylaminocarbonyl-1-phenyl-3,5-dihydro-2,3-benzodiazepin-4(4H)-one To a solution of 7,8-methylenedioxy-1-phenyl-3,5-dihydro-2,3-benzodiazepin-4(4H)-one (130 mg, 0.46 mmol) in CH$_2$Cl$_2$ (5 ml) was added triethylamine (1 mL), DMAP (5 mg) and methylisocyanate (60 mg) and the mixture was stirred at 25° C. for 24 h. The reaction mixture was then poured into a separatory funnel containing water (50 mL) and the product was extracted with CH$_2$Cl$_2$ (3×40 mL). The combined extracts were dried over Na$_2$SO$_4$ and solvent removed in vacuo. Purification of the residue by chromatography (1:1 of ethyl acetate: hexane) resulted in the product as a white solid (92 mg, 59%), mp, 180°–182.5° C. $^1$H NMR (CDCl$_3$) 8.60 (bs, 1H), 7.74 (m, 2H), 7.46 (m, 3H), 6.88 (s, 1H), 6.67 (s, 1H), 6.07 (bs, 1H), 6.03 (bs, 1H), 3.54 (s, 1H) 3.54 (s, 1H), 2.93 (s, 1.5H), 2.92 (s, 1.5H).

EXAMPLE 16

7,8-Methylenedioxy-3-methyl-1-phenyl-3,5-dihydro-2,3-benzodiazepin-4(4H)-one Method a: To a solution of 7,8-methylenedioxy-1-phenyl-3,5-dihydro-2,3-benzodiazepin-4(4H)-one (50 mg, 0.18 mmol) in DMF (3 mL) was added MeI (0.1 mL) and K$_2$CO$_3$ (200 mg) and the mixture was stirred at 25° C. for 3 hours. The K$_2$CO$_3$ was removed by filtration. The solvent was then removed in vacuo and the residue was purified by chromatography to give the product as a white solid (42 mg, 80%), mp, 168°–172° C. $^1$H NMR (CDCl$_3$) 7.62 (m, 2H), 7.43 (m, 3H), 6.86 (s, 1H), 6.63 (s, 1H), 6.03 (bs, 2H), 3.44 (s, 3H), 3.43 (bm, 2H).

Method b: A mixture of methyl 2-benzoyl-4,5-methylenedioxyphenylacetate (300 mg) and methylhydrazine (0.2 mL) in 2-methoxyethanol (5 mL) was heated to reflux for 87 h. The reaction mixture was then cooled to 25° C. and the solvent was removed in vavuo. The residue was purified by chromatography to give the product which was further purified by recrystallization.

EXAMPLE 17

3-Ethyl-7,8-methylenedioxy-1-phenyl-3,5-dihydro-2,3-benzodiazepin-4(4H)-one

The title compound was prepared using the same method as Example 16, method a, as a white solid, yield 92%, mp, 150°–152° C. $^1$H NMR (CDCl$_3$) 7.62 (m, 2H), 7.43 (m, 3H), 6.03 (bs, 2H), 3.90 (bm, 2H), 3.52 (bm, 1H), 3.30 (bm, 1H), 1.24 (t, J=7.1, 3H).

EXAMPLE 18

3-Isopropyl-7,8-methylenedioxy-1-phenyl-3,5-dihydro-2,3-benzodiazepin-4(4H)-one The title compound was prepared using the same method as Example 16, method a, as a white solid, yield 90%, mp, 167°–168° C. $^1$H NMR (CDCl$_3$) 7.65 (m, 2H), 7.44 (m, 3H), 6.85 (s, 1H), 6.65 (s, 1H), 6.04 (bs, 1H), 6.01 (bs, 1H), 4.91 (heptet, J=6.6, 1H), 3.53 (bd, J=11.6, 1H), 3.24 (bd, J=11.6, 1H), 1.49 (bs, 1.5H), 1.48 (bs, 1.5H), 1.14 (bs, 1.5H), 1.13 (bs, 1.5H).

EXAMPLE 19

3-(2-Hydroxyethyl)-7,8-methylenedioxy-3,5-dihydro-2,3-benzodiazepin-4(4H)-one The title compound was prepared using the same method as Example 16, method b, as a white solid, yield 17%, mp, 159°–161° C. $^1$H NMR (CDCl$_3$) 7.59 (m, 2H), 7.44 (m, 3H), 6.86 (s, 1H), 6.63 (s, 1H), 4.10 (bm, 2H), 3.93 (bs, 2H), 3.50 (bm, 2H), 3.00 (bs, 1H).

EXAMPLE 20

3-Isopropyl-1-(4-methylphenyl)-7,8-methylenedioxy-3,5-dihydro-2,3-benzodiazepin-4(4H)-one The title compound was prepared using the same method as Example 16, method a, as a white solid, yield 95%. $^1$H NMR (CDCl$_3$) 7.53 (m, 2H), 7.23 (m, 3H), 6.84 (s, 1H), 6.64

(s, 1H), 6.04 (bs, 1H), 5.99 (bs, 1H), 4.89 (heptet, J=6.7, 1H), 3.51 (bd, J=12.1, 1H), 3.22 (bd, J=12.1, 1H), 2.41 (s, 3H), 1.48 (bs, 1.5H), 1.47 (bs, 1.5H), 1.13 (bs, 1.5H), 1.11 (bs, 1.5H).

EXAMPLE 21

3-(2-Butyl)-7,8-methylenedioxy-1-phenyl-3,5-dihydro-2,3-benzodiazepin-4(4H)-one The title compound was prepared using the same method as Example 16, method a, as a white solid, yield 73%, mp, 140°–143° C. $^1$H NMR (CDCl$_3$) 7.64 (m, 2H), 7.43 (m, 3H), 6.86 (s, 1H), 6.64 (s, 1H), 6.05 (bs, 1H), 6.01 (bs, 1H), 4.70 (bm, 1H), 3.54 (bd, J=11.8, 1H), 3.26 (bd, J=11.8, 1H), 2.10 (bs, 0.5H), 1.75 (bs, 0.5H), 1.05 (m, 1H), 1.48 (bs, 1H), 1.46 (bs, 1H), 1.10 (bm, 1H), 0.97 (bm, 1H), 0.57 (bm, 2H).

EXAMPLE 22

7,8-Methylenedioxy-3-(3-pentyl)-1-phenyl-3,5-dihydro-2,3-benzodiazepin-4(4H)-one The title compound was prepared using the same method as Example 16, method a, as a white solid, mp, 145°–147° C. $^1$H NMR (CDCl$_3$) 7.64 (m, 2H), 7.43 (m, 3H), 6.87 (s, 1H), 6.64 (s, 1H), 6.05 (bs, 1H), 6.02 (bs, 1H), 4.55 (heptet, J=4.9, 1H), 3.56 (bd, J=12.6, 1H), 3.29 (bd, J=12.6, 1H), 2.10 (bm, 1H), 1.75 (bm, 1H), 1.51 (bm, 2H), 0.98 (bs, 3H), 0.51 (bs, 3H).

EXAMPLE 23

7,8-Methylenedioxy-1-(4-nitrophenyl)-3-(3-pentyl)-3,5-dihydro-2,3-benzodiazepin-4(4H)-one The title compound was prepared using the same method (59%) as Example 16, method a, as a white solid, mp, 173°–175° C. $^1$H NMR (CDCl$_3$) 8.28 (d, J=8.7, 2H), 7.82 (d, J=8.7, 2H), 6.89 (s, 1H), 6.58 (s, 1H), 6.06 (bs, 2H), 4.60 (m, 1H), 3.60 (m, 1H), 3.29 (m 1H), 2.05 (bm, 1H), 1.75 (bm, 1H), 1.51 (bm, 2H), 0.98 (bs, 3H), 0.51 (bs, 3H).

EXAMPLE 24

7,8-Methylenedioxy-3-(1-pentyl)-1-phenyl-3,5-dihydro-2,3-benzodiazepin-4(4H)-one The title compound was prepared using the same method (89%) as Example 16, method a, as a white solid, mp, 95°–97° C. $^1$H NMR (CDCl$_3$) 7.62 (m, 2H), 7.43 (m, 3H), 6.86 (s, 1H), 6.63 (s, 1H), 6.03 (bs, 2H), 4.01 (m, 1H), 3.75 (m, 1H), 3.52 (m, 1H), 3.33 (m, 1H), 1.64 (pentet, J=7.1, 2H), 1.29 (pentet, 2H), 1.22 (m, 2H), 0.84 (t, J=6.9, 3H).

EXAMPLE 25

7,8-Methylenedioxy-3-(2-pentyl)-1-phenyl-3,5-dihydro-2,3-benzodiazepin-4(4H)-one The title compound was prepared using the same method (90%) as Example 16, method a, as a white solid, mp, 138°–140° C. $^1$H NMR (CDCl$_3$) 7.64 (m, 2H), 7.43 (m, 3H), 6.86 (s, 1H), 6.64 (s, 1H), 6.05 (bs, 1H), 6.03 (bs, 1H), 4.76 (m, 1H), 3.52 (m, 1H), 3.25 (m, 1H), 2.15–0.70 (m, 10H).

EXAMPLE 26

3-Benzyl-7,8-methylenedioxy-1-phenyl-3,5-dihydro-2,3-benzodiazepin-4(4H)-one The title compound was prepared using the same method (86%) as Example 16, method a, as a white solid, mp, 134°–137° C. $^1$H NMR (CDCl$_3$) 7.50–7.21 (m, 10H), 6.88 (s, 1H), 6.56 (s, 1H), 6.04, (bs, 2H), 5.33 (m, 1H), 4.85 (m, 1H), 3.60 (m, 1H), 3.40 (m, 1H).

EXAMPLE 27

1-(4-Aminophenyl)-7,8-methylenedioxy-3-(3-penty)-3,5-dihydro-2,3-benzodiazepin-4(4H)-one To a solution of 7,8-methylenedioxy-1-(4-nitrophenyl)-3-(3-pentyl)-3,5-dihydro-2,3-benzodiazepin-4(4H)-one (48 mg, 0.123 mmol) in ethanol (10 mL) was added hydrazine hydrate (0.5 mL), 3 drops of conc. HCl, and excess amount of Raney Ni and the mixture obtained was stirred at room temperature for 1.5 h. Then the Raney Ni was removed by decanting. The crude product obtained by removal of the solvent was purified by flash chromatography (1:1 of hex:EtOAc) to give the product (42 mg, 94%), $^1$H NMR (CDCl$_3$) 7.46 (d, J=8.3, 2H), 6.69 (d, J=8.3, 2H), 6.85 (s, 1H), 6.70 (s, 1H), 6.04, (bs, 1H), 6.01 (bs, 1H), 4.49 (heptet, J=4.9, 1H), 3.92 (bs, 2H), 3.50 (d, J=16.3, 1H), 3.29 (d, J=16.3, 1H), 2.10 (m, 1H), 1.72 (m, 1H), 1.48 (m, 21H), 0.98 (t, J=7.2, 3H), 0.48 (t, J=7.2, 3H).

EXAMPLE 28

3-Cyclopentyl-7,8-methylenedioxy-1-phenyl-3,5-dihydro-2,3-benzodiazepin-4(4H)-one The title compound was prepared using the same method (69%) as Example 16, method a, as a white solid, mp, 135°–143° C. $^1$H NMR (CDCl$_3$) 7.62 (m, 2H), 7.43 (m, 3H), 6.85 (s, 1H), 6.64 (s, 1H), 6.03 (bs, 11H), 6.00 (bs, 1H), 5.12 (pentet, J=7.5, 1H), 3.53 (d, J=12.6, 1H), 3.24 (d, J=12.6, 1H), 2.22–1.45 (m, 8H).

EXAMPLE 29

3-(4-Heptyl)-7,8-methylenedioxy-1-phenyl-3,5-dihydro-2,3-benzodiazepin-4(4H)-one The title compound was prepared using the same method (85%) as Example 16, method a, as a white solid, mp, 135°–143° C., $^1$H NMR (CDCl$_3$) 7.62 (m, 2H), 7.43 (m, 3H), 6.85 (s, 1H), 6.64 (s, 1H), 6.03 (bs, 1H), 6.00 (bs, 1H), 5.12 (pentet, J=7.5, 1H), 3.53 (d, J=12.6, 1H), 3.24 (d, J=12.6, 1H), 2.20–1.60 (m, 14H).

EXAMPLE 30

3-Cycloheptyl-7,8-methylenedioxy-1-phenyl-3,5-dihydro-2,3-benzodiazepin-4(4H)-one The title compound was prepared using the same method (85%) as Example 16, method a, as a white solid, mp, 166°–169° C. $^1$H NMR (CDCl$_3$) 7.62 (m, 2H), 7.45 (m, 3H), 6.86 (s, 1H), 6.63 (s, 1H), 6.04 (bs, 1H), 6.00 (bs, 1H), 4.68 (m, 1H), 3.53 (m, 1H), 2.30–1.40 (m, 12H).

EXAMPLE 31

3-Cyclohexyl-7,8-methylenedioxy-1-phenyl-3,5-dihydro-2,3-benzodiazepin-4(4H)-one The title compound was prepared using the same method (40%) as Example 16, method a, as a white solid, mp, 195°–197° C. $^1$H NMR (CDCl$_3$) 7.62 (m, 2H), 7.43 (m, 3H), 6.85 (s, 1H), 6.63 (s, 1H), 6.04 (bs, 1H), 6.00 (bs, 1H), 4.49 (m, 1H), 3.53 (d, J=12.6, 1H), 3.24 (d, J=12.6, 1H), 2.15–1.20 (m, 10H).

EXAMPLE 32

3-Cyclohexylmethyl-7,8-methylenedioxy-1-phenyl-3,5-dihydro-2,3-benzodiazepin-4(4H)-one The title compound was prepared using the same method (34%) as Example 16, method a, as a white solid, mp, 153°–157° C. $^1$H NMR (CDCl$_3$) 7.62 (m, 2H), 7.43 (m, 3H), 6.87 (s, 1H), 6.62 (s, 1H), 6.04 (bs, 2H), 4.05 (bm, 1H), 3.57–3.29 (bm, 3H), 1.80–0.75 (m, 10H).

EXAMPLE 33

3-(3-Hexyl)-7,8-methylenedioxy-1-phenyl-3,5-dihydro-2,3-benzodiazepin-4(4H)-one

The title compound was prepared using the same method (85%) as Example 16, method a, as a white solid, mp, 129°–132° C. $^1$H NMR (CDCl$_3$) 7.62 (m, 2H), 7.43 (m, 3H), 6.86 (s, 1H), 6.63 (s, 1H), 6.04 (bs, 2H), 4.63 (m, 1H), 4.05 (bm, 1H), 3.54 (d, J=12.7, 1H), 3.27 (d, J=12.7, 1H), 2.20–0.45 (m, 12H).

EXAMPLE 34

3-(4-Methoxybenzyl)-7,8-methylenedioxy-1-phenyl-3,5-dihydro-2,3-benzodiazepin-4(4H)-one The title compound was prepared using the same method (75%) as Example 16, method a, as a white solid, mp, 115°–118° C. $^1$H NMR (CDCl$_3$) 7.50 (m, 2H), 7.39 (m, 3H), 7.17 (d, J=8.4, 2H), 6.86 (s, 1H), 6.79 (d, J=8.4, 2H), 6.56 (s, 1H), 6.02 (bs, 2H), 5.22(m, 1H), 4.80 (m, 1H), 3.76 (s, 3H), 3.55 (m, 2H).

EXAMPLE 35

3-(2-Dimethylaminoethyl)-7,8-methylenedioxy-1-phenyl-3,5-dihydro-2,3-benzodiazepin-4(4H)-one The title compound was prepared using the same method (79%) as Example 16, method a, as a white solid, mp, 130°–132° C. $^1$H NMR (CDCl$_3$) 7.63 (m, 2H), 7.45 (m, 3H), 6.85 (s, 1H), 6.63 (s, 1H), 6.03 (bs, 2H), 4.00 (m, 2H), 2.62 (t, J=6.8, 2H), 2.28 (s, 6H).

EXAMPLE 36

3-(2-Diethylaminoethyl)-7,8-methylenedioxy-1-phenyl-3,5-dihydro-2,3-benzodiazepin-4(4H)-one Hydrochloride The free base, 1-phenyl-7,8-methylenedioxy-3-(2-diethylaminoethyl)-2,3-benzodiazepin-4(3H)-one, was prepared using the same method as Example 16, method a. The title compound was obtained by treating the free base with conc. hydrochloric acid in ethanol. $^1$H NMR (D$_2$O) 7.65 (m, 2H), 7.55 (m, 3H), 7.04 (s, 1H), 6.85 (s, 1H), 6.08 (bs, 2H), 4.50 (m, 1H), 4.10 (m, 1H), 3.70–3.40 (m, 4H), 3.14 (m, 4H), 1.25–1.05 (m, 6H).

EXAMPLE 37

7,8-Methylenedioxy-3-(2-morpholinoethyl)-1-phenyl-3,5-dihydro-2,3-benzodiazepin-4(4H)-one The title compound was prepared using the same method (83%) as Example 16, method a, as a white solid, $^1$H NMR (CDCl$_3$) 7.63 (m, 2H), 7.45 (m, 3H), 6.86 (s, 1H), 6.63 (s, 1H), 6.03 (bs, 2H), 4.20–3.85 (m, 2H), 3.61–3.25 (m, 2H), 2.61 (t, J=6.8, 2H), 2.44 (bs, 4H).

EXAMPLE 38

7,8-Methylenedioxy-3-(4-nitrophenyl)-1-phenyl-3,5-dihydro-2,3-benzodiazepin-4(4H)-one The title compound was prepared using the same method as Example 16, method a, yield 61%, mp>200° C.

EXAMPLE 39

3-(4-Aminophenyl)-7,8-methylenedioxy-1-phenyl-3,5-dihydro-2,3-benzodiazepin-4(4H)-one To a solution of 7,8-methylenedioxy-3-(4-nitrophenyl)-1-phenyl-3,5-dihydro-2,3-benzodiazepin-4(4H)-one (15 mg, 0.037 mmol) in ethanol (5 mL) was added HCl (conc. 2 drops), hydrazine hydrate (0.3 mL) and Raney Ni (excess) and the reaction was stirred for 40 min. The excess Raney Ni was removed by filtration and the pure product (9 mg, 66%) was obtained by flash chromatography (12.5% acetone in CH$_2$Cl$_2$). $^1$H NMR (CDCl$_3$) 7.60 (m, 2H), 7.42 (m, 3H), 7.20 (d, J=8.6, 2H), 6.92 (s, 1H), 6.71 (d, J=8.6, 2H), 6.68 (s, 1H), 6.07 (s, 1H), 6.03 (s, 1H), 3.80–3.45 (m, 4H).

EXAMPLE 40

Methyl 2-(3,4-Methylenedioxyphenyl)propionate

To a solution of LDA in THF (60 mL) was added methyl 3,4-methylenedioxyphenylacetate (2 g, 10.3 mmol) at −78° C. and the solution was warmed to −15° C. for 45 min. MeI (4.39 g, 30.9 mmol) was added and the reaction was warmed to room temperature for 16 h. The reaction mixture was then poured to a separatory funnel containing NH$_4$Cl (80 mL) and the product was extracted with EtOAc (2×150 mL) and dried over Na$_2$SO$_4$. The crude product obtained by removal of the solvent was purified by flash chromatography to give the product as a colorless solid (1.36 g , 63%). $^1$H NMR (CDCl$_3$) 6.75 (m, 3H), 5.95 (s 2H), 3.67 (s, 3H), 3.66 (m, 1H), 1.46 (d, J=7.4, 3H).

EXAMPLE 41

Methyl 2-(2-Benzoyl-4,5-methylenedioxyphenyl)propionate

To a solution of methyl 2-(3,4-methylenedioxyphenyl)propionate (1.04 g, 5 mmol) in CH$_2$Cl$_2$ (30 mL) at 0° C. was added SnCl$_4$ (1M solution in CH$_2$Cl$_2$, 9 mL, 9 mmol). Then a solution of benzoyl chloride (1 mL) in CH$_2$Cl$_2$ (10 mL) was added dropwise and the mixture obtained was warmed to 25° C. for 20 h with stirring. The reaction mixture was poured into a separatory funnel containing Na$_2$CO$_3$ solution (sat. 50 mL) and some ice. The organic layer was separated and the aqueous was extracted with CH$_2$Cl$_2$ (3×50 mL). The combined extracts were washed with water (50 mL), NaHCO$_3$ (sat. 40 mL) and brine (50 mL) and dried over Na$_2$SO$_4$. The pure product (360 mg, 23%) was obtained by chromatography on silica gel (hexane/ethyl acetate=4:1). $^1$H NMR (CDCl$_3$) 7.80–7.45 (m, 5H), 6.96 (s, 1H), 6.79 (s, 1H), 6.03 (s, 2H) 3.70 (m, 1H), 3.58 (s, 3H), 1.47 (d, J=7.4, 3H).

EXAMPLE 42

5-Methyl-7,8-methylenedioxy-1-phenyl-3,5-dihydro-2,3-benzodiazepin-4(4H)-one

A mixture of methyl 2-(2-benzoyl-4,5-methylenedioxyphenyl)propionate, hydrazine hydrate (0.45 mL), and 2-methoxyethanol (6 mL) was heated to reflux for 20 h. The solvent was then removed in vacuo and the residue was purified by a flash chromatography (EtOAc:Hex=1:1.5) to yield the product as a white solid (62 mg, 18%), mp, 206°–209° C. $^1$H NMR (CDCl$_3$) 8.45 (s, 1H), 7.62 (m, 2H), 7.45 (m, 3H), 6.88 (s, 1H), 6.63 (s, 1H), 6.05 (s, 1H), 6.00 (s, 1H), 3.29 (q,J=6.7, 1H), 1.62 (d,J=6.7, 3H).

EXAMPLE 43

3-Methyl-7,8-methylenedioxy-1-phenyl-3,5-dihydro-2,3-benzodiazepin-4(4H)-one-2-N-oxide To a solution of 7,8-methylenedioxy-3-methyl-1-phenyl-3,5-dihydro-2,3-benzodiazepin-4(4H)-one (30 mg, 0.102 mmol) in CH$_2$Cl$_2$ (10 mL) was added MCPBA (100 mg) and the reaction was stirred at room temperature for 72 h. The reaction mixture was washed with NaHCO$_3$ (10 mL) and dried over Na$_2$SO$_4$. The crude product thus obtained was purified by a flash chromatography (EtOAc:Hex=3:7) to yield the pure product as a white solid (10 mg, 33%), mp, 194°–197° C. $^1$H NMR (CDCl$_3$) 7.71 (m, 2H), 7.44 (m, 3H), 6.85 (s, 1H), 6.48 (s, 1H), 6.05 (s, 1H), 6.00 (s, 1H), 3.77 (d, J=13.7, 1H), 3.59 (d, J=13.7, 1H), 3.37 (s, 3H).

EXAMPLE 44

Methyl 2-(2-(4-nitrobenzoyl)-4,5-methylenedioxyphenyl)propionate

To a mixture of methyl 2-(3,4-methylenedioxyphenyl) propionate (1.0 g, 4.8 mmol), 4-nitrobenzoic acid (1.6 g, 9.6 mmol) and 1,2-dichloroethane (35 mL) was added P$_2$O$_5$ (4 g) and the mixture obtained was heated to reflux for 12 h. Water was added to the reaction mixture and it was neutralized to pH=7–8 by NaHCO$_3$ solution. It was extracted with EtOAc and washed with brine. The product (211 mg, 12.3%) was obtained by a chromatographic purification (EtOAc:Hex=1:4). $^1$H NMR (CDCl$_3$) 8.31 (d, J=8.7, 2H), 7.94 (d, J=8.7, 2H), 7.00 (s, 1H), 6.73 (s, 1H), 6.06 (s, 2H) 4.15 (q, J=7.1, 1H), 3.59 (s, 3H), 1.51 (d, J=7.1, 3H).

EXAMPLE 45

1-(4-Aminophenyl)-5-methyl-7,8-methylenedioxy-3,5-dihydro-2,3-benzodiazepin-4(4H)-one A mixture of methyl 2-(2-(4-nitrobenzoyl)-4,5-methylenedioxyphenyl)propionate (211 mg, 0.59 mmol), hydrazine hydrate (0.15 mL, 2.4 mmol), and 2-methoxyethanol (6 mL) was heated to reflux for 72 h. The solvent was removed in vacuo and the crude product was purified by chromatography to yield 7,8-methylenedioxy-5-methyl-1-(4-nitrophenyl)-3,5-dihydro-2,3-benzodiazepin-4(4H)-one which was treated with excess amount of hydrazine and Raney Ni for 1 h. The reaction was then allowed to settled and liquid phase was decanted. The solvent was then removed and residue obtained was purified by chromatography (10% acetone in CH$_2$Cl$_2$) to yield the product (5 mg). $^1$H NMR (CDCl$_3$) 8.44 (s, 1H), 7.43 (d, J=8.7, 2H), 6.86 (s, 1H), 6.68 (d, J=8.7, 2H), 6.65 (s, 1H), 6.04 (s, 1H), 6.00 (s, 1H), 4.83 (b, 2H), 3.29 (q, J=6.8, 1H), 1.59 (d, J=6.8, 3H).

EXAMPLE 46

3-Methylaminocarbonyl-7,8-methylenedioxy-1-(4-nitrophenyl)-3,5-dihydro-2,3-benzodiazepin-4(4H)-one The title compound was prepared using the same method as Example 15, yield, 53%, mp, 298°–300° C.

EXAMPLE 47

Methyl 2-(2-(3,4-Methylenedioxybenzoyl)-4,5-methylenedioxyphenyl)propionate

To a mixture of methyl 2-(3,4-methylenedioxyphenyl) propionate (1 g, 4.8 mmol) in 1,2-dichloroethane (50 mL) was added piperonylic acid (1.6 g, 9.6 mmol) and P$_2$O$_5$ (4 g). The reaction mixture was stirred for 15 h and then poured to ice water (200 mL) and the product was extracted with EtOAc (2×100 mL). The pure product was obtained by flash chromatography (453 mg, 27%). $^1$H NMR (CDCl$_3$) 7.37 (s, 1H), 7.33 (d, J=8.0, 1H), 6.95 (s, 1H), 6.83 (d, J=8.0, 1H), 6.76 (s, 1H), 6.07 (s, 2H), 6.02 (s, 2H), 3.95 (q, J=7.1, 1H), 3.58 (s, 3H), 1.45 (d, J=7.1, 3H).

EXAMPLE 48

5-Methyl-1-(3,4-methylenedioxyphenyl)-7,8-methylenedioxy-3,5-dihydro-2,3-benzodiazepin-4(4H)-one The title compound was made according to the procedure in Example 42, yield: 10%.

EXAMPLE 49

3-(2-Aminoethyl)-7,8-methylenedioxy-1-phenyl-3,5-dihydro-2,3-benzodiazepin-4(4H)-one The intermediate 3-cyanomethyl-7,8-methylenedioxy-1-phenyl-3,5-dihydro-2,3-benzodiazepin-4(4H)-one was made according to the procedure described in Example 16, method a. This unstable compound was reduced to the title compound according the procedure described in Example 27, yield, 71%. $^1$H NMR (CDCl$_3$), 7.61 (m, 2H), 7.42 (m, 3H), 6.86 (s, 1H), 6.63 (s, 1H), 6.03 (bs, 2H), 3.95 (bm, 2H), 3.40 (bm, 2H), 2.97 (bm, 2H), 1.4 (b, 2H).

EXAMPLE 50

1-[4-(Isopropylamino)phenyl]-7,8-methylenedioxy-3,5-dihydro-2,3-benzodiazepin-4(4H)-one To a solution of 1-(4-aminophenyl)-7,8-methylenedioxy-3,5-dihydro-2,3-benzodiazepin-4(4H)-one (110 mg, 0.373 mmol) in DMF (3 mL) was added 2-iodopropane (290 μL, 2.91 mmol). The mixture was stirred at 65° C. for two days, diluted with EtOAc (45 mL), washed with water and brine, dried over Na$_2$SO$_4$ and concentrated in vacuo. The residue was purified by chromatography to afford the title compound as a tan solid (60 mg, 0.18 mmol, 48%), mp: 144°–146° C. $^1$H NMR (CDCl$_3$) 8.20 (s, 1H), 7.41 (d, J=8.5, 2H), 6.81 (s, 1H), 6.74 (s, 1H), 6.56 (d, J=8.5, 2H), 6.02 (s, 2H), 3.80 (s, 1H), 3.69 (m, 1H), 3.42 (s, 2H), 1.24 (d, J=6.0, 6H).

EXAMPLE 51

Methyl 4,5-Methylenedioxy-2-(3-nitrobenzoyl) phenylacetate

The title compound was prepared from methyl 3,4-methylenedioxyphenylacetate (368 mg, 1.89 mmol) in ClCH$_2$CH$_2$Cl (8 mL), 3-nitrobenzoic acid (393 mg, 2.35 mmol) and P$_2$O$_5$ (3.2 g) as a yellow oil (500 mg, 1.46 mmol, 77%). $^1$H NMR (CDCl$_3$) 8.60 (s, 1H), 8.43 (d, J=7.8, 1H), 8.13 (d, J=7.8, 1H), 7.68 (t, J=7.8, 1H), 6.86 (s, 1H), 6.82 (s, 1H), 6.07 (s, 2H), 3.87 (s, 2H), 3.63 (s, 3H).

EXAMPLE 52

Methyl 4,5-Methylenedioxy-2-(3-methoxy-4-nitrobenzoyl)phenylacetate

The title compound was prepared from methyl 3,4-methylenedioxyphenylacetate (1.6 g, 8.0 mmol) in ClCH$_2$CH$_2$Cl (50 mL), 3-methoxy-4-nitrobenzoic acid (1.8 g, 9.3 mmol) and P$_2$O$_5$ (4 g) as a light yellow solid (1.2 g, 3.2 mmol, 40%). $^1$H NMR (CDCl$_3$) 7.84 (d, J=8.2, 1H), 7.54 (d, J=1.4, 1H), 7.32 (dd, J=8.2, 1.4, 1H), 6.85 (s, 2H), 6.07 (s, 2H), 4.00 (s, 3H), 3.85 (s, 2H), 3.64 (s, 3H).

EXAMPLE 53

Methyl 4,5-Methylenedioxy-2-(3-methyl-4-nitrobenzoyl)phenylacetate

The title compound was prepared from methyl 3,4-methylenedioxyphenylacetate (2.1 g, 11 mmol) in ClCH$_2$CH$_2$Cl (70 mL), 3-methyl-4-nitrobenzoic acid (3.7 g, 20 mmol) and P$_2$O$_5$ (6 g) as an oily solid (1.4 g, 3.9 mmol, 35%). $^1$H NMR (CDCl$_3$) 7.99 (d, J=8.2, 1H), 7.74 (s, 1H), 6.69 (d, J=8.2, 1H), 6.84 (s, 1H), 6.83 (s, 1H), 6.07 (s, 2H), 3.86 (s, 2H), 3.64 (s, 3H), 2.63 (s, 3H).

EXAMPLE 54

Methyl 2-(2-Chloro-4-nitrobenzoyl)-4,5-methylenedioxyphenylacetate

The title compound was prepared from methyl 3,4-methylenedioxyphenylacetate (12.5 g, 64.4 mmol) in ClCH$_2$CH$_2$Cl (150 mL), 2-chloro-4-nitrobenzoic acid (25.0 g, 124 mmol) and P$_2$O$_5$ (37 g) as a yellow solid (11 g, 29 mmol, 45%). $^1$H NMR (CDCl$_3$) 8.15 (s, 1H), 8.14 (d, J=8.4, 1H), 7.58 (d, J=8.4, 1H), 6.84 (s, 1H), 6.71 (s, 1H), 6.05 (s, 2H), 4.03 (s, 2H), 3.73 (s, 3H).

EXAMPLE 55

7,8-Methylenedioxy-1-(3-nitrophenyl)-3,5-dihydro-2,3-benzodiazepin-4(4H)-one

The title compound was prepared from methyl 4,5-methylenedioxy-2-(3-nitrobenzoyl)phenylacetate (500 mg, 1.46 mmol), hydrazine hydrate (350 µL, 6.20 mmol), and acetic acid (50 µL) in ethanol (15 mL) as a yellow solid (30 mg, 0.092 mmol, 6%), mp: 251°–253° C. $^1$H NMR (CDCl$_3$) 8.52 (s, 1H), 8.46 (s, 1H), 8.31 (d, J=8.2, 1H), 7.99 (d, J=8.2, 1H), 7.62 (t, J=8.2, 1H), 6.87 (s, 1H), 6.57 (s, 1H), 6.06 (s, 2H), 3.49 (s, 2H). Anal. Calcd. for C$_{16}$H$_{11}$N$_3$O$_5$: C, 59.08; H, 3.41; N, 12.92. Found: C, 58.95; 11, 3.29; N, 12.15.

EXAMPLE 56

7,8-Methylenedioxy-1-(3-methoxy-4-nitrophenyl)-3,5-dihydro-2,3-benzodiazepin-4(4H)-one The title compound was prepared from methyl 4,5-methylenedioxy-2-(3-methoxy-4-nitrobenzoyl)phenylacetate (1.2 g, 3.2 mmol) and hydrazine hydrate (0.6 mL, 11 mmol) in ethanol (15 mL) as a yellow solid (0.53 g, 1.5 mmol, 47%), mp: 267°–269° C. $^1$H NMR (CDCl$_3$) 8.60 (s, 1H), 7.86 (d, J=8.5, 1H), 7.49 (d, J=1.5, 1H), 7.13 (dd, J=8.5, 1.5, 1H), 6.85 (s, 1H), 6.59 (s, 1H), 6.06 (s, 2H), 4.01 (s, 3H), 3.48 (s, 2H). Anal. Calcd. for C$_{17}$H$_{13}$N$_3$O$_6$: C, 57.47; H, 3.69; N, 11.83. Found: C, 57.07; H, 3.42; N, 12.01.

EXAMPLE 57

7,8-Methylenedioxy-1-(3-methyl-4-nitrophenyl)-3,5-dihydro-2,3-benzodiazepin-4(4H)-one The title compound was prepared from methyl 4,5-methylenedioxy-2-(3-methyl-4-nitrobenzoyl)phenylacetate (1.4 g, 3.9 mmol) and hydrazine hydrate (1.0 mL, 18 mmol) in ethanol (25 mL) as a yellow solid (0.65 g, 1.9 mmol, 49%), mp: 275°–277° C. $^1$H NMR (CDCl$_3$) 8.65 (s, 1H), 8.02 (d, J=8.5, 1H), 7.62 (s, 1H), 7.56 (d, J=8.5, 1H), 6.85 (s, 1H), 6.56 (s, 1H), 6.06 (s, 2H), 3.48 (s, 2H), 2.64 (s, 3H). Anal. Calcd. for C$_{17}$H$_{13}$N$_3$O$_5$: C, 60.18; H, 3.86; N, 12.38. Found: C, 60.22; H, 3.83; N, 12.28.

EXAMPLE 58

1-(2-Chloro-4-nitrophenyl)-7,8-methylenedioxy-3,5-dihydro-2,3-benzodiazepin-4(4H)-one The title compound was prepared from methyl 4,5-methylenedioxy-2-(2-chloro-4-nitrobenzoyl)phenylacetate (11 g, 29 mmol) and hydrazine hydrate (5.0 mL, 88 mmol) in ethanol (60 mL) as a yellow solid (1.4 g, 3.9 mmol, 13%), mp: 202°–204° C. $^1$H NMR (CDCl$_3$) 8.64 (s, 1H), 8.29–8.26 (m, 2H), 7.82 (d, J=8.2, 1H), 6.84 (s, 1H), 6.28 (s, 1H), 6.02 (s, 2H), 3.59 (s, 2H). Anal. Calcd. for C$_{16}$H$_{10}$N$_3$O$_5$·(½)H$_2$O: C, 52.12; H, 3.01; N, 11.40. Found: C, 52.50; H, 3.36; N, 10.35.

EXAMPLE 59

1-(3-Aminophenyl)-7,8-methylenedioxy-3,5-dihydro-2,3-benzodiazepin-4(4H)-one

To a suspension of 7,8-methylenedioxy-1-(3-nitrophenyl)-3,5-dihydro-2,3-benzodiazepin-4(4H)-one (20 mg, 0.061 mmol) in ethanol (5 ml,) was added Raney Ni (54 mg), hydrazine hydrate (40 µL, 0.71 mmol), and 2N HCl (60 µL, 0.12 mmol). The mixture was stirred at room temperature for 24 h. The solid Ni was filtered out. The filtrate was concentrated in vacuo and the resulting residue was purified by chromatography (10:1 CHCl$_3$/EtOH) to afford the title compound as a tan solid (6 mg, 33%), mp: 118°–122° C. $^1$H NMR (CDCl$_3$) 8.33 (s, 1H), 7.22–7.17 (m, 1H), 6.94 (s, 1H), 6.94–6.88 (m, 1H), 6.81 (s, 1H), 6.79–6.75 (m, 1H), 6.67 (s, 1H), 6.03 (s, 2H), 3.74 (brs, 2H), 3.44 (s, 2H).

EXAMPLE 60

1-(4-Amino-3-methoxyphenyl)-7,8-methylenedioxy-3,5-dihydro-2,3-benzodiazepin-4(4H)-one To a solution of 7,8-methylenedioxy-1-(3-methoxy-4-nitrophenyl)-3,5-dihydro-2,3-benzodiazepin-4(4H)-one (136 mg, 0.387 mmol) in acetone (6 mL) was added ethanol (3 mL), water (4 mL), 5% Pd/C (33 mg) and HCO$_2$NH$_4$ (240 mg, 3.81 mmol). The mixture was stirred at room temperature for 3 h. The catalyst was filtered out. The filtrate was concentrated in vacuo and the resulting residue was collected by filtration, washed with water, and dried in vacuo to afford the title compound as a light yellow solid (98 mg, 0.31 mmol, 80%), mp: 147°–150° C. $^1$H NMR (CDCl$_3$) 8.32 (s, 1H), 7.24 (d, J=1.9, 1H), 6.87 (dd, J=1.9, 8.0, 1H), 6.82 (s, 1H), 6.73 (s, 1H), 6.02 (s, 2H), 4.08 (s, 2H), 3.90 (s, 3H), 3.43 (s, 211). Anal. calcd. for C$_{17}$H$_{15}$N$_3$O$_4$·(⅜)H$_2$O: C, 61.49; H, 4.78; N, 12.65. Found: C, 61.33; H, 4.39; N, 12.54.

EXAMPLE 61

1-(4-Amino-3-methylphenyl)-7,8-methylenedioxy-3,5-dihydro-2,3-benzodiazepin-4(4H)-one To a suspension of 7,8-methylenedioxy-1-(3-methyl-4-nitrophenyl)-3,5-dihydro-2,3-benzodiazepin-4(4H)-one (147 mg, 0.433 mmol) in ethanol (5 mL) was added water (2.5 mL), 5% Pd/C (42 mg), and HCO$_2$NH$_4$ (320 mg, 5.07 mmol). The mixture was stirred at room temperature for 4 h.

The catalyst was filtered out. The filtrate was concentrated in vacuo and water (25 mL) was then added to the residue. The resulting solid was collected by filtration, washed with water, and dried in vacuo to afford the title compound as a light yellow solid (65 mg, 0.21 mmol, 49%), mp: 164°–166° C. $^1$H NMR (CDCl$_3$) 8.23 (s, 1H), 7.35–7.22 (m, 2H), 6.82 (s, 1H), 6.71–6.65 (m, 2H), 6.03 (s, 2H), 3.87 (s, 2H), 3.42 (s, 2H), 2.19 (s, 2H). Anal. calcd. for $C_{17}H_{15}N_3O_3 \cdot H_2O$: C, 62.38; H, 5.23; N, 12.84. Found: C, 62.50; H, 5.19; N, 12.86.

EXAMPLE 62

1-(4-Amino-2-chlorophenyl)-7,8-methylenedioxy-3,5-dihydro-2,3-benzodiazepin-4(4H)-one To a suspension of 7,8-methylenedioxy-1-(2-chloro-4-nitrophenyl)-3,5-dihydro-2,3-benzodiazepin-4(4H)-one (1.4 g, 3.9 mmol) in 1:1:1 ethanol/acetone/water (45 mL) was added 5% Pd/C (106 mg) and HCO$_2$NH$_4$ (2.5 g, 40 mmol). The mixture was stirred at room temperature for 3 h and 15 mL of ethanol was added to the mixture which was then stirred at room temperature for three days. The catalyst was filtered out. The filtrate was extracted with EtOAc (100 mL). The organic phase was washed with water and brine, dried over Na$_2$SO$_4$ and concentrated in vacuo. The residue was purified by chromatography (1:4 hexane/EtOAc) to afford the title compound as a light yellow solid (0.27 g, 0.82 mmol, 21%), mp: 238°–240° C. $^1$H NMR (CDCl$_3$) 8.34 (s, 1H), 7.41 (d, J=8.6, 1H), 6.81 (s, 1H), 6.69–6.67 (m, 3H), 6.02 (s, 2H), 3.92 (s, 2H), 3.42 (s, 2H).

EXAMPLE 63

1-(4-Amino-3-chlorophenyl)-7,8-methylendioxy-3,5-dihydro-2,3-benzodiazepin-4(4H)-one To a solution of 1-(4-aminophenyl)-7,8-methylenedioxy-3,5-dihydro-2,3-benzodiazepin-4(4H)-one (118 mg, 0.400 mmol) in DMF (3 mL) was added NCS (51 mg, 0.38 mmol). The mixture was stirred at room temperature for 20 h, diluted with EtOAc (50 mL), washed with water and brine, dried over Na$_2$SO$_4$ and concentrated in vacuo. The residue was purified by chromatography (1:1 hexane/EtOAc) to afford the title compound as a tan solid (60 mg, 0.18 mmol, 45%), mp: 256°–258° C. $^1$H NMR (CDCl$_3$) 8.50 (s, 1H), 7.54 (s, 1H), 7.32 (d, J=8.3, 1H), 6.82 (s, 1H), 6.77 (d, J=8.3, 1H), 6.69 (s, 1H), 6.04 (s, 2H), 4.33 (s, 2H), 3.42 (s, 2H).

EXAMPLE 64

1-(4-Amino-3,5-dichlorophenyl)-7,8-methylenedioxy-3,5-dihydro-2,3-benzodiazepin-4(4H)-one To a solution of 1-(4-aminophenyl)-7,8-methylenedioxy-3,5-dihydro-2,3-benzodiazepin-4(4H)-one (116 mg, 0.393 mmol) in 4:1 MeCN/DMF (5 mL) was added NCS (101 mg, 0.756 mmol). The mixture was stirred at room temperature for 5 h, diluted with EtOAc (50 mL), washed with water and brine, dried over Na$_2$SO$_4$ and concentrated in vacuo. The residue was purified by chromatography (1:1 hexane/EtOAc) to afford the title compound as a tan solid (50 mg, 0.14 mmol, 35%), mp: 149°–151° C. $^1$H NMR (CDCl$_3$) 8.57 (s, 1H), 7.47 (s, 2H), 6.82 (s, 1H), 6.67 (s, 1H), 6.05 (s, 2H), 4.72 (s, 2H), 3.42 (s, 2H).

EXAMPLE 65

1-(4-Amino-3,5-dibromophenyl)-7,8-methylenedioxy-3,5-dihydro-2,3-benzodiazepin-4(4H)-one To a solution of 1-(4-aminophenyl)-3,5-dihydro-7,8-methylenedioxy4H-2,3-benzodiazepin-4-one (20 mg, 0.068 mmol) in MeCN (3 mL) was added NBS (27 mg, 0.15 mmol). The mixture was stirred at room temperature for 0.5 h, diluted with EtOAc (20 mL), washed with water and brine, dried over Na$_2$SO$_4$ and concentrated in vacuo to afford the title compound as a tan solid (14 mg, 0.031 mmol, 46%), mp: 162°–165° C. $^1$H NMR (CDCl$_3$) 8.32 (s, 1H), 7.66 (s, 2H), 6.82 (s, 1H), 6.68 (s, 1H), 6.05 (s, 2H), 4.83 (s, 2H), 3.41 (s, 2H).

EXAMPLE 66

1-(4-Azidophenyl)-7,8-methylenedioxy-3,5-dihydro-2,3-benzodiazpin-4(4H)-one

To a solution of 1-(4-aminophenyl)-7,8-methylenedioxy-3,5-dihydro-2,3-benzodiazepin-4(4H)-one (114 mg, 0.386 mmol) in CF$_3$CO$_2$H (3 mL) was added NaNO$_2$ (66 mg, 0.96 mmol) at 0° C. The mixture was stirred at 0° C. for 0.5 h., and then NaN$_3$ (296 mg, 3.95 mmol) was added. The mixture was further stirred at 0° C. for 0.5 h, diluted with EtOAc (20 mL), washed with water, saturated NaHCO$_3$ and brine, dried over Na$_2$SO$_4$ and concentrated in vacuo to afford the title compound as a yellow solid (110 mg, 0.342 mmol, 89%), mp: 158°–160° C. $^1$H NMR (CDCl$_3$) 8.45 (s, 1H), 7.60 (d, J=8.4, 2H), 7.07 (d, J=8.4, 2H), 6.83 (s, 1H), 6.61 (s, 1H), 6.04 (s, 2H), 3.45 (s, 2H).

EXAMPLE 67

1-(4-Acetamidophenyl)-7,8-methylenedioxy-3,5-dihydro-2,3-benzodiazepin-4(4H)-one To a suspension of 1-(4-aminophenyl)-7,8-methylenedioxy-3,5-dihydro-2,3-benzodiazepin-4-(4H)-one (90 mg, 0.30 mmol) in CH$_2$Cl$_2$ (10 mL) was added Ac$_2$O (0.30 mL, 3.2 mmol) and Et$_3$N (0.60 mL, 4.3 mmol) at room temperature. The mixture was stirred at room temperature for 2 h, diluted with EtOAc (40 mL), washed with water, 2N NaOH water and brine, dried over Na$_2$SO$_4$ and concentrated in vacuo. The residue was purified by chromatography to afford the title compound as a white solid (70 mg, 0.21 mmol, 70%), mp: 177°–180° C. $^1$H NMR (CDCl$_3$) 8.34 (s, 1H), 7.57 (s, 4H), 7.27 (s, 1H), 6.83 (s, 1H), 6.64 (s, 1H), 6.03 (s, 2H), 3.45 (s, 2H), 2.22 (s, 3H). Anal. calcd. for $C_{18}H_{15}N_3O_4 \cdot (\frac{1}{2})H_2O$: C, 62.42; H, 4.66; N, 12.13. Found: C, 62.60; H, 4.62; N, 11.57.

EXAMPLE 68

7,8-Methylenedioxy-1-(4-ureidophenyl)-3,5-dihydro-2,3-benzodiazepin-4(4H)-one

To a solution of 1-(4-aminophenyl)-7,8-methylenedioxy-3,5-dihydro-2,3-benzodiazepin-4(4H)-one (119 mg, 0.403 mmol) in acetic acid (2 mL) was added NaOCN (38 mg, 0.58 mmol) at room temperature. The mixture was stirred at room temperature for 4 h, diluted with EtOAc (80 mL), washed with 2 N NaOH, water and brine, dried over Na$_2$SO$_4$ and concentrated in vacuo. The residue was purified by chromatography to afford the title compound as a yellow solid (40 mg, 0.12 mmol, 30%), mp: 238°–241° C. $^1$H NMR (DMSO-d$_6$) 10.79 (s, 1H), 8.77 (s, 1H), 7.47 (d, J=8.7, 2H), 7.40 (d, J=8.7, 2H), 7.07 (s, 1H), 6.61 (s, 1H), 6.10 (s, 2H), 5.95 (s, 2H), 3.33 (s, 2H).

EXAMPLE 69

7,8-Methylenedioxy-1-(4-thioureidophenyl)-3,5-dihydro-2,3-benzodiazepin-4(4H)-one To a solution of 1-(4-aminophenyl)-7,8-methylenedioxy-3,5-dihydro-2,3-benzodiazepin-4(4H)-one (127 mg, 0.430 mmol) in acetic acid (2 mL) was added NaSCN (103 mg, 1.06 mmol) at room temperature. The mixture was stirred at 95° C. for 5 h, diluted with EtOAc (50 mL), washed with water, 2N NaOH, water and brine, dried over $Na_2SO_4$ and concentrated in vacuo. The residue was purified by chromatography to afford the title compound as a yellow solid (10 mg, 0.028 mmol, 7%), mp: 236°–238° C. $^1$H NMR (DMSO-$d_6$) 10.88 (s, 1H), 9.88 (s, 1H), 7.52 (d, J=8.7, 2H), 7.46 (d, J=8.7, 2H), 7.08 (s, 1H), 6.62 (s, 1H), 6.10 (s, 2H), 3.30 (s, 2H).

The potency of antagonism or positive modulation for the compounds of Example 9, 14, 15, 18, 21, 22, 25, 30, 31, 33, 45, 48, 56, 61, 62 and 63 described above in AMPA receptors expressed in oocytes and their anticonvulsant activity against maximal electroshock are shown in Table 1.

TABLE 1

| Example # | AMPA antagonism $IC_{50}$ ($\mu$M) | AMPA positive potentiation 200% @ $\mu$M | MES $ED_{50}$ mg/kg (iv) |
|---|---|---|---|
| 9 | 15 | | |
| 14 | 3 | | 2.4 |
| 15 | 26 | | |
| 45 | 4 | | |
| 48 | 10 | | |
| 56 | 20 | | |
| 61 | 1 | | 2.7 |
| 62 | 4 | | 3.2 |
| 63 | 0.8 | | |
| 18 | | 30 | |
| 21 | | 12 | |
| 22 | | 11 | |
| 25 | | 160 | |
| 30 | | 10 | |
| 31 | | 11 | |
| 33 | | 24 | |

The ability of AMPA receptor antagonists or positive modulators to inhibit or enhance AMPA induced current in oocyte expressing neuronal AMPA receptor was determined using procedures fully described in Keana et al, *J. Med. Chem.* 38: 4367–4379 (1995). Compounds of examples 14, 61 and 62 are antagonists of AMPA receptor with a potency of 3, 1 and 4 $\mu$M, respectively, and are active as anticonvulsants in the MES experiment. The compounds of examples 22, 30 and 31 are positive modulators of AMPA receptor. They potentiate the AMPA current 200% at a concentration of 11, 10 and 11 $\mu$M, respectively.

Having now fully described this invention, it will be understood by those of ordinary skill in the art that the same can be performed within a wide and equivalent range of conditions, formulations and other parameters without affecting the scope of the invention or any embodiment thereof. All patents, patent applications and publications cited herein are fully incorporated by reference herein in their entirety.

What is claimed is:

1. A compound having the Formula I:

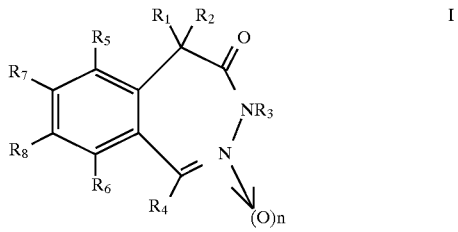

or a pharmaceutically acceptable salt or hemisuccinate ester thereof, wherein:

$R_1$ and $R_2$ are independently hydrogen, alkyl, haloalkyl, aryl, fused aryl, a carbocyclic group, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, aminoalkyl or thioalkyl; or $R_1$ and $R_2$ are taken together to form a carbocycle or heterocycle;

$R_3$ is hydrogen, alkyl, haloalkyl, aryl, fused aryl, a carbocyclic group, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, aminoalkyl, COR, $CO_2R$ or $CONR_xR_y$, wherein R, $R_x$ and $R_y$ are independently hydrogen, alkyl, haloalkyl, aryl, fused aryl, carbocyclic, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl or aminoalkyl; or $R_x$ and $R_y$ are taken together to form a carbocycle or heterocycle;

$R_4$ is substituted or unsubstituted aryl, fused aryl, a carbocyclic group, a heterocyclic group, or a heteroaryl group;

$R_5$ and $R_6$ are independently hydrogen, halo, haloalkyl, aryl, fused aryl, a carbocyclic group, a heterocyclic group, a heteroaryl group, alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, nitro, amino, cyano, acylamido, hydroxy, thiol, acyloxy, azido, alkoxy, carboxy, carbonylamido or alkylthiol;

$R_7$ and $R_8$ are independently haloalkyl, aryl, fused aryl, a carbocyclic group, a heterocyclic group, a heteroaryl group, alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, nitro, amino, cyano, acylamido, thiol, acyloxy, azido, carboxy, carbonylamido or alkylthiol; or $R_7$ and $R_8$ taken together form a carbocycle or heterocycle; and n is 0 or 1.

2. A compound according to claim 1, wherein $R_1$ and $R_2$ are independently hydrogen, alkyl, haloalkyl, aryl, fused aryl, a carbocyclic group, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, aminoalkyl or thioalkyl; and $R_3$ is hydrogen, alkyl, haloalkyl, aryl, fused aryl, a carbocyclic group, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, aminoalkyl, COR, $CO_2R$ or $CONR_xR_y$, wherein R, $R_x$ and $R_y$ are independently hydrogen, alkyl, haloalkyl, aryl, fused aryl, carbocyclic, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl or aminoalkyl.

3. A compound according to claim 1, wherein $R_7$ and $R_8$ are taken together to form a carbocycle or heterocycle.

4. A compound according to claim 1, wherein $R_7$ and $R_8$ taken together are —$OCH_2O$—, —$(CH_2)_3$—, —$(CH_2)_4$—, —$OCH_2CH_2O$—, —$CH_2N(R)CH_2$—, —$CH_2CH_2N(R)CH_2$—, —$CH_2N(R)CH_2CH_2$—, or —N═C—C═N—.

5. A compound according to claim 1, wherein $R_7$ and $R_8$ taken together is —N(Me)—C(O)—O—.

6. A compound according to claim 1, wherein $R_4$ is substituted or unsubstituted aryl or heteroaryl.

7. A compound according to claim 1, wherein $R_3$ is hydrogen, COR, $CO_2R$ or $CONR_xR_y$.

8. A compound according to claim 1, wherein $R_3$ is $C_{3-10}$ alkyl, arylalkyl, heteroarylalkyl, a carbocyclic group, carbocycloalkyl, a heterocyclic group, or a heterocycloalkyl group.

9. A compound according to claim 1, said compound selected from the group consisting of:

7,8-methylenedioxy-1-phenyl-3,5-dihydro-2,3-benzodiazepin-4(4H)-one, 7,8-ethylenedioxy-1-phenyl-3,5-dihydro-2,3-benzodiazepin-4(4H)-one, 1-phenyl-cyclopenta[h]-3,5-dihydro-2,3-benzodiazepin-4(4H)-one, 3-methylaminocarbonyl-7,8-methylenedioxy-1-phenyl-3,5-dihydro-2,3-benzodiazepin-4(4H)-one, 1-(4-aminophenyl)-7,8-methylenedioxy-3,5-dihydro-2,3-benzodiazepin-4(4H)-one, 1-(4-aminophenyl)-6-chloro-7,8-methylenedioxy-3,5-dihydro-2,3-benzodiazepin-4(4H)-one, 1-(4-aminophenyl)-9-chloro-7,8-methylenedioxy-3,5-dihydro-2,3-benzodiazepin-4(4H)-one, 1-(4-isopropylaminophenyl)-7,8-methylenedioxy-3,5-dihydro-2,3-benzodiazepin-4(4H)-one, 7,8-methylenedioxy-1-(4-methylphenyl)-3,5-dihydro-2,3-benzodiazepin-4(4H)-one, 7,8-methylenedioxy-1-(4-methoxyphenyl)-3,5-dihydro-2,3-benzodiazepin-4(4H)-one, 1-(3-aminophenyl)-7,8-methylenedioxy-3,5-dihydro-2,3-benzodiazepin-4(4H)-one, 1-(4-hydroxyphenyl)-7,8-methylenedioxy-3,5-dihydro-2,3-benzodiazepin-4(4H)-one, 1-(4-amino-3-methylphenyl)-7,8-methylenedioxy-3,5-dihydro-2,3-benzodiazepin-4(4H)-one, 1-(4-amino-3-chlorophenyl)-7,8-methylenedioxy-3,5-dihydro-2,3-benzodiazepin-4(4H)-one, 1-(4-aminophenyl)-5-methyl-7,8-methylenedioxy-3,5-dihydro-2,3-benzodiazepin-4(4H)-one, 1-(4-amino-2-chlorophenyl)-7,8-methylenedioxy-3,5-dihydro-2,3-benzodiazepin-4(4H)-one, 7,8-methylenedioxy-1-(3,4-methylenedioxyphenyl)-3,5-dihydro-2,3-benzodiazepin-4(4H)-one, 7,8-methylenedioxy-1-(3,4-methylenedioxyphenyl)-5-methyl-3,5-dihydro-2,3-benzodiazepin-4(4H)-one, 1-(4-acetamidophenyl)-7,8-methylenedioxy-5-methyl-3,5-dihydro-2,3-benzodiazepin-4(4H)-one, 1-(4-azidophenyl)-7,8-methylenedioxy-3,5-dihydro-2,3-benzodiazepin-4(4H)-one, 1-(4-methylaminophenyl)-7,8-methylenedioxy-3,5-dihydro-2,3-benzodiazepin-4(4H)-one, 3-cycloheptyl-7,8-methylenedioxy-1-phenyl-3,5-dihydro-2,3-benzodiazepin-4(4H)-one, 3-(3-hexyl)-7,8-methylenedioxy-1-phenyl-3,5-dihydro-2,3-benzodiazepin-4(4H)-one, 7,8-methylenedioxy-3-(2-pentyl)-1-phenyl-3,5-dihydro-2,3-benzodiazepin-4(4H)-one, 3-cyclohexyl-7,8-methylenedioxy-1-phenyl-3,5-dihydro-2,3-benzodiazepin-4(4H)-one, 3-cyclopentyl-7,8-methylenedioxy-1-phenyl-3,5-dihydro-2,3-benzodiazepin-4(4H)-one, 3-isopropyl-7,8-methylenedioxy-1-phenyl-3,5-dihydro-2,3-benzodiazepin-4(4H)-one, 3-(2-butyl)-7,8-methylenedioxy-1-phenyl-3,5-dihydro-2,3-benzodiazepin-4(4H)-one, and 7,8-methylenedioxy-3-(3-pentyl)-1-phenyl-3,5-dihydro-2,3-benzodiazepin-4(4H)-one;

or a pharmaceutically acceptable salt or hemisuccinate ester thereof.

10. A compound of claim 1 having the formula V:

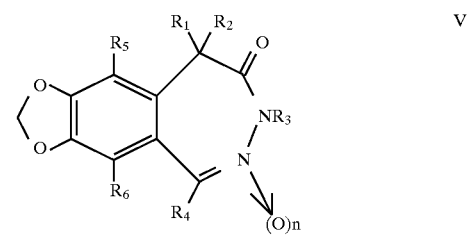

or a pharmaceutically acceptable salt or hemisuccinate ester thereof.

11. A compound of claim 1 having the formula VI:

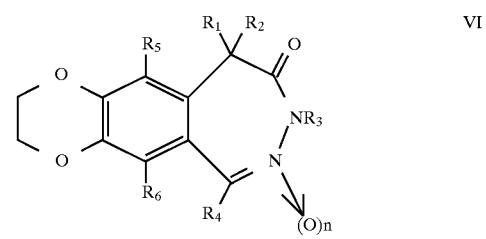

or a pharmaceutically acceptable salt or hemisuccinate ester thereof.

12. A compound of claim 1 having the formula VII:

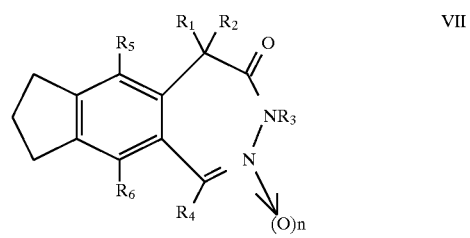

or a pharmaceutically acceptable salt or hemisuccinate ester thereof.

13. A compound of claim 1 having the formula VIII:

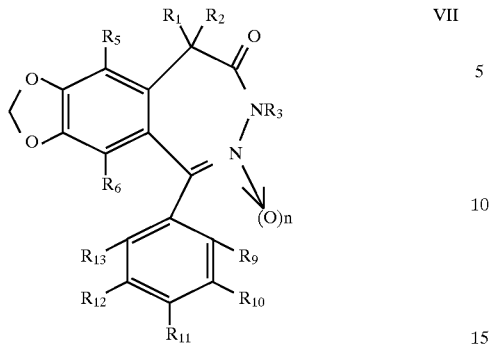

or a pharmaceutically acceptable salt or hemisuccinate ester thereof wherein $R_1$–$R_3$, $R_5$–$R_6$ and n are as defined previously with respect to Formula I; and $R_9$–$R_{13}$ are independently hydrogen, halo, haloalkyl, aryl, fused aryl, carbocyclic, a heterocyclic group, a heteroaryl group, alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, nitro, amino, cyano, acylamido, hydroxy, thiol, acyloxy, azido, alkoxy, carboxy, carbonylamido or alkylthiol.

14. A compound according to claim 13, wherein $R_{10}$ and $R_{11}$ are taken together to form a carbocycle or heterocycle.

15. A compound according to claim 13, wherein $R_{10}$ and $R_{11}$ taken together are —$OCH_2O$—, —$(CH_2)_3$—, —$(CH_2)_4$—, —$OCH_2CH_2O$—, —$CH_2N(R)CH_2$—, —$CH_2CH_2N(R)CH_2$—, —$CH_2N(R)CH_2CH_2$— or —N=C—C=N—.

16. A compound according to claim 13, wherein $R_{10}$ and $R_{11}$ taken together is —N(Me)—C(O)—O—.

17. A pharmaceutical composition comprising the compound of any one of claims 1–16 and a pharmaceutically acceptable carrier.

18. A method of treating, or ameliorating neuronal loss associated with stroke, ischemia, CNS trauma, hypoglycemia or surgery; or treating or ameliorating a neurodegenerative disease selected from the group consisting of Alzheimer's disease, amyotrophic lateral sclerosis, Huntington's disease, Parkinson's disease and Down's syndrome; or treating, or ameliorating the adverse consequences of the overstimulation of the excitatory amino acids; or treating or ameliorating anxiety, psychosis, convulsions, chronic pain, glaucoma, urinary incontinence or inducing anesthesia; or enhancing cognition; or treating or ameliorating schizophrenia; comprising administering to an animal in need of such treatment an effective amount of a compound having the Formula I:

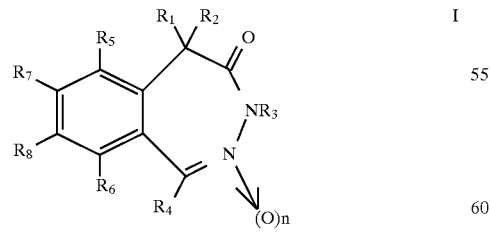

or a pharmaceutically acceptable salt or hemisuccinate ester thereof, wherein:

$R_1$ and $R_2$ are independently hydrogen, alkyl, haloalkyl, aryl, fused aryl, a carbocyclic group, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, aminoalkyl or thioalkyl; or $R_1$ and $R_2$ are taken together to form a carbocycle or heterocycle;

$R_3$ is hydrogen, alkyl, haloalkyl, aryl, fused aryl, a carbocyclic group, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, aminoalkyl, COR, $CO_2R$ or $CONR_xR_y$, wherein R, $R_x$ and $R_y$ are independently hydrogen, alkyl, haloalkyl, aryl, fused aryl, carbocyclic, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl or aminoalkyl; or $R_x$ and $R_y$ are taken together to form a carbocycle or heterocycle;

$R_4$ is substituted and unsubstituted aryl, fused aryl, a carbocyclic group, a heterocyclic group, or a heteroaryl group;

$R_5$ and $R_6$ are independently hydrogen, halo, haloalkyl, aryl, fused aryl, carbocyclic, a heterocyclic group, a heteroaryl group, alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, nitro, amino, cyano, acylamido, hydroxy, thiol, acyloxy, azido, alkoxy, carboxy, carbonylamido or alkylthiol;

$R_7$ and $R_8$ are independently, haloalkyl, aryl, fused aryl, a carbocyclic group, a heterocyclic group, a heteroaryl group, alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, nitro, amino, cyano, acylamido, thiol, acyloxy, azido, carboxy, carbonylamido or alkylthiol; or $R_7$ and $R_8$ are taken together to form a carbocycle or heterocycle; and n is 0 or 1.

19. The method according to claim 18, wherein $R_1$ and $R_2$ are independently hydrogen, alkyl, haloalkyl, aryl, fused aryl, a carbocyclic group, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, aminoalkyl or thioalkyl; and $R_3$ is hydrogen, alkyl, haloalkyl, aryl, fused aryl, a carbocyclic group, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, aminoalkyl, COR, $CO_2R$ or $CONR_xR_y$, wherein R, $R_x$ and $R_y$ are independently hydrogen, alkyl, haloalkyl, aryl, fused aryl, carbocyclic, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl or aminoalkyl.

20. The method of claim 18, wherein $R_7$ and $R_8$ taken together are —$OCH_2O$—, —$(CH_2)_3$—, —$(CH_2)_4$—, —$OCH_2CH_2O$—, —$CH_2N(R)CH_2$—, —$CH_2CH_2N(R)CH_2$—, —$CH_2N(R)CH_2CH_2$— or —N=C—C=N—.

21. The method of claim 18, wherein $R_7$ and $R_8$ taken together is —N(Me)—C(O)—O—.

22. A method of treating, or ameliorating global ischemia and neuronal degeneration, comprising administering to an animal in need thereof an effective amount of a compound having the Formula I:

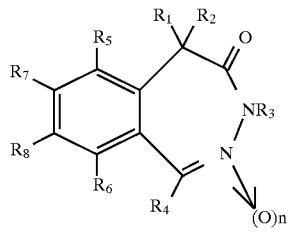

or a pharmaceutically acceptable salt or hemisuccinate ester thereof, wherein:

$R_1$ and $R_2$ are independently hydrogen, alkyl, haloalkyl, aryl, fused aryl, a carbocyclic group, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, aminoalkyl or thioalkyl; or $R_1$ and $R_2$ are taken together to form a carbocycle or heterocycle;

$R_3$ is hydrogen, alkyl, haloalkyl, aryl, fused aryl, a carbocyclic group, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, aminoalkyl, COR, $CO_2R$ or $CONR_xR_y$, wherein R, $R_x$ and $R_y$ are independently hydrogen, alkyl, haloalkyl, aryl, fused aryl, carbocyclic, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl or aminoalkyl; or $R_x$ and $R_y$ are taken together to form a carbocycle or heterocycle;

$R_4$ is substituted and unsubstituted aryl, fused aryl, a carbocyclic group, a heterocyclic group, or a heteroaryl group;

$R_5$ and $R_6$ are independently hydrogen, halo, haloalkyl, aryl, fused aryl, a carbocyclic group, a heterocyclic group, a heteroaryl group, alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, nitro, amino, cyano, acylamido, hydroxy, thiol, acyloxy, azido, alkoxy, carboxy, carbonylamido or alkylthiol;

$R_7$ and $R_8$ are independently, haloalkyl, aryl, fused aryl, a carbocyclic group, a heterocyclic group, a heteroaryl group, alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, nitro, amino, cyano, acylamido, thiol, acyloxy, azido, carboxy, carbonylamido or alkylthiol; or $R_7$ and $R_8$ are taken together to form a carbocycle or heterocycle; and n is 0 or 1.

23. The method according to claim 22, wherein $R_1$ and $R_2$ are independently hydrogen, alkyl, haloalkyl, aryl, fused aryl, a carbocyclic group, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, aminoalkyl or thioalkyl; and $R_3$ is hydrogen, alkyl, haloalkyl, aryl, fused aryl, a carbocyclic group, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, aminoalkyl, COR, $CO_2R$ or $CONR_xR_y$, wherein R, $R_x$ and $R_y$ are independently hydrogen, alkyl, haloalkyl, aryl, fused aryl, carbocyclic, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl or aminoalkyl.

24. The method of claim 22, wherein $R_7$ and $R_8$ taken together are —$OCH_2O$—, —$(CH_2)_3$—, —$(CH_2)_4$—, —$OCH_2CH_2O$—, —$CH_2N(R)CH_2$—, —$CH_2CH_2N(R)CH_2$—, —$CH_2N(R)CH_2CH_2$— or —N=C—C=N—.

25. The method of claim 22, wherein $R_7$ and $R_8$ taken together is —N(Me)—C(O)—O—.

26. The method of claim 22, wherein said neuronal degeneration is a result of amyotrophic lateral sclerosis.

27. A method of treating, or ameliorating schizophrenia, comprising administering to an animal in need thereof an effective amount of a compound having the Formula I:

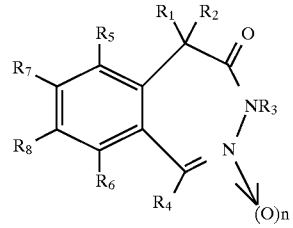

or a pharmaceutically acceptable salt or hemisuccinate ester thereof, wherein:

$R_1$ and $R_2$ are independently hydrogen, alkyl, haloalkyl, aryl, fused aryl, a carbocyclic group, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, aminoalkyl or thioalkyl; or $R_1$ and $R_2$ are taken together to form a carbocycle or heterocycle;

$R_3$ is hydrogen, alkyl, haloalkyl, aryl, fused aryl, a carbocyclic group, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, aminoalkyl, COR, $CO_2R$ or $CONR_xRy$, wherein R, $R_x$ and $R_y$ are independently hydrogen, alkyl, haloalkyl, aryl, fused aryl, carbocyclic, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl or aminoalkyl; or $R_x$ and $R_y$ are taken together to form a carbocycle or heterocycle;

$R_4$ is substituted and unsubstituted aryl, fused aryl, a carbocyclic group, a heterocyclic group, or a heteroaryl group;

$R_5$ and $R_6$ are independently hydrogen, halo, haloalkyl, aryl, fused aryl, a carbocyclic group, a heterocyclic group, a heteroaryl group, alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, nitro, amino, cyano, acylamido, hydroxy, thiol, acyloxy, azido, alkoxy, carboxy, carbonylamido or alkylthiol;

$R_7$ and $R_8$ are independently haloalkyl, aryl, fused aryl, a carbocyclic group, a heterocyclic group, a heteroaryl group, alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, nitro, amino, cyano, acylamido, thiol, acyloxy, azido, carboxy, carbonylamido or alkylthiol; or R₇ and R₈ are taken together to form a carbocycle or heterocycle; and n is 0 or 1.

28. The method according to claim 27, wherein

R₁ and R₂ are independently hydrogen, alkyl, haloalkyl, aryl, fused aryl, a carbocyclic group, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, aminoalkyl or thioalkyl; and R₃ is hydrogen, alkyl, haloalkyl, aryl, fused aryl, a carbocyclic group, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, aminoalkyl, COR, CO₂R or CONR$_x$R$_y$, wherein R, R$_x$ and R$_y$ are independently hydrogen, alkyl, haloalkyl, aryl, fused aryl, carbocyclic, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl or aminoalkyl.

29. The method of claim 27, wherein R₇ and R₈ taken together are —OCH₂O—, —(CH₂)₃—, —(CH₂)₄—, —OCH₂CH₂O—, —CH₂N(R)CH₂—, —CH₂CH₂N(R)CH₂—, —CH₂N(R)CH₂CH₂— or —N=C—C=N—.

30. The method of claim 27, wherein R₇ and R₈ taken together is —N(Me)—C(O)—O—.

31. A method of treating or ameliorating the adverse consequences of hypostimulation of the excitatory amino acids; enhancing cognition; treating or ameliorating malnutrition and neural maldevelopment; treating or ameliorating neurodegenerative diseases including Alzheimer's disease, amyotrophic lateral sclerosis, Huntington's disease, Parkinson's disease and Down's syndrome, or treating or ameliorating schizophrenia; comprising administering to an animal in need of such treatment an effective amount of a compound having the Formula I:

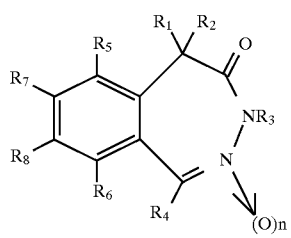

or a pharmaceutically acceptable salt or hemisuccinate ester thereof wherein

R₁ and R₂ are independently hydrogen, alkyl, haloalkyl, aryl, fused aryl, a carbocyclic group, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, aminoalkyl or thioalkyl; or R₁ and R₂ are taken together to form a carbocycle or heterocycle;

R₃ is alkyl, haloalkyl, a carbocyclic group, a heterocyclic group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, or aminoalkyl;

R₄ is substituted and unsubstituted aryl, fused aryl, a carbocyclic group, a heterocyclic group, or a heteroaryl group;

R₅ and R₆ are independently hydrogen, halo, haloalkyl, aryl, fused aryl, a carbocyclic group, a heterocyclic group, a heteroaryl group, alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, nitro, amino, cyano, acylamido, hydroxy, thiol, acyloxy, azido, alkoxy, carboxy, carbonylamido or alkylthiol;

R₇ and R₈ are independently, haloalkyl, aryl, fused aryl, a carbocyclic group, a heterocyclic group, a heteroaryl group, alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, nitro, amino, cyano, acylamido, thiol, acyloxy, azido, carboxy, carbonylamido or alkylthiol; or R₇ and R₈ are taken together to form a carbocycle or heterocycle; and n is 0 or 1.

32. The method according to claim 31, wherein

R₁ and R₂ are independently hydrogen, alkyl, haloalkyl, aryl, fused aryl, a carbocyclic group, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, aminoalkyl or thioalkyl.

33. The method of claim 31, wherein R₇ and R₈ taken together are —OHC₂O—, —(CH₂)₃—, —(CH₂)₄—, —OCH₂CH₂O—, —CH₂N(R)CH₂—, —CH₂CH₂N(R)CH₂—, —CH₂N(R)CH₂CH₂— or —N=C—C=N—.

34. The method of claim 31, wherein R₇ and R₈ taken together is —N(Me)—C(O)—O—.

35. A method of treatment according to claim 31, said compound selected from the group consisting of:

3-cycloheptyl-7,8-methylenedioxy-1-phenyl-3,5-dihydro-2,3-benzodiazepin-4(4H)-one, 3-(3-hexyl)-7,8-methylenedioxy-1-phenyl-3,5-dihydro-2,3-benzodiazepin-4(4H)-one, 7,8-methylenedioxy-3-(2-pentyl)-1-phenyl-3,5-dihydro-2,3-benzodiazepin-4(4H)-one, 3-cyclohexyl-7,8-methylenedioxy-1-phenyl-3,5-dihydro-2,3-benzodiazepin-4(4H)-one, 3-cyclopentyl-7,8-methylenedioxy-1-phenyl-3,5-dihydro-2,3-benzodiazepin-4(4H)-one, 3-isopropyl-7,8-methylenedioxy-1-phenyl-3,5-dihydro-2,3-benzodiazepin-4(4H)-one, 3-(2-butyl)-7,8-methylenedioxy-1-phenyl-3,5-dihydro-2,3-benzodiazepin-4(4H)-one, and 7,8-methylenedioxy-3-(3-pentyl)-1-phenyl-3,5-dihydro-2,3-benzodiazepin-4(4H)-one;

or a pharmaceutically acceptable salt or hemisuccinate ester thereof.

36. A method for the preparation of the compound represented by formula I:

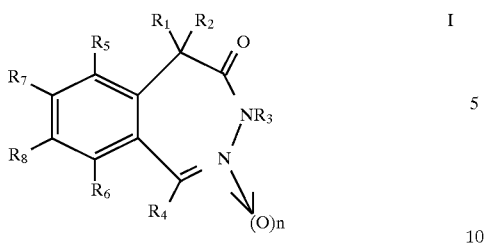

or a pharmaceutically acceptable salt or hemisuccinate ester thereof, wherein:

$R_1$ and $R_2$ are independently hydrogen, alkyl, haloalkyl, aryl, fused aryl, a carbocyclic group, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, aminoalkyl or thioalkyl; or $R_1$ and $R_2$ are taken together to form a carbocycle or heterocycle;

$R_3$ is hydrogen, alkyl, haloalkyl, aryl, fused aryl, a carbocyclic group, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, aminoalkyl, COR, $CO_2R$ or $CONR_xR_y$, wherein R, $R_x$ and $R_y$ are independently hydrogen, alkyl, haloalkyl, aryl, fused aryl, carbocyclic, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl and aminoalkyl; or $R_x$ and $R_y$ are taken together to form a carbocycle or heterocycle;

$R_4$ is substituted and unsubstituted aryl, fused aryl, a carbocyclic group, a heterocyclic group, or a heteroaryl group;

$R_5$ and $R_6$ are independently hydrogen, halo, haloalkyl, aryl, fused aryl, a carbocyclic group, a heterocyclic group, a heteroaryl group, alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, nitro, amino, cyano, acylamido, hydroxy, thiol, acyloxy, azido, alkoxy, carboxy, carbonylamido or alkylthiol;

$R_7$ and $R_8$ are independently hydrogen, halo, haloalkyl, aryl, fused aryl, a carbocyclic group, a heterocyclic group, a heteroaryl group, alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, nitro, amino, cyano, acylamido, hydroxy, thiol, acyloxy, azido, alkoxy, carboxy, carbonylamido or alkylthiol; or $R_7$ and $R_8$ are taken together to form a carbocycle or heterocycle; and n is 0 or 1; comprising the steps of:

(a) reacting, in the presence of a catalyst, a compound of Formula II

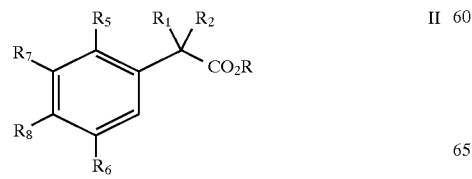

wherein R is lower alkyl and $R_1$–$R_2$, $R_5$–$R_8$ are as defined previously in formula I, with a compound of Formula III

wherein X is OH or halogen and $R_4$ is as defined previously in formula I, to afford a compound of Formula IV

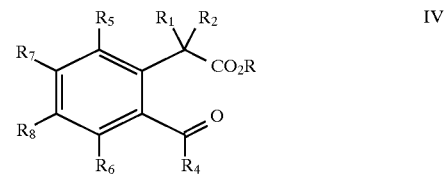

wherein $R_1$–$R_2$, $R_4$–$R_8$ and R are as defined previously in formula I; and (b) reacting the compound of Formula IV with $H_2NNHR_3$, wherein $R_3$ is as previously defined in Formula 1, to afford the compound of Formula I wherein n=0; and (c) optionally, when $R_3$ is hydrogen, reacting the compound of Formula I with $XR_3$, wherein X is a leaving group, in the presence of a base, to afford the compound of Formula I; and (d) optionally, when n=0, reacting a compound of formula I with $H_2O_2$ or peracid, to afford a compound of formula I wherein n=1.

37. The method according to claim 36, wherein $R_1$ and $R_2$ are independently hydrogen, alkyl, haloalkyl, aryl, fused aryl, a carbocyclic group, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, aminoalkyl or thioalkyl; and $R_3$ is hydrogen, alkyl, haloalkyl, aryl, fused aryl, a carbocyclic group, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, aminoalkyl, COR, $CO_2R$ or $CONR_xR_y$, wherein R, $R_x$ and $R_y$ are independently hydrogen, alkyl, haloalkyl, aryl, fused aryl, carbocyclic, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl or aminoalkyl.

38. The method of claim 36, wherein the catalyst is a Lewis acid.

39. The method of claim 38, wherein the Lewis acid is $SnCl_4$ or $P_2O_5$.

40. The method of claim 36, wherein $R_7$ and $R_8$ form —$OCH_2O$—, —$(CH_2)_3$—, —$(CH_2)_4$—, —$OCH_2CH_2O$—, —$CH_2N(R)CH_2$—, —$CH_2CH_2N(R)CH_2$—, —$CH_2N(R)CH_2CH_2$— or N=C—C=N—.

41. The method of claim 36, wherein $R_7$ and $R_8$ form —N(Me)—C(O)—O—.

* * * * *